US009566269B2

(12) United States Patent
Kalofonos et al.

(10) Patent No.: US 9,566,269 B2
(45) Date of Patent: Feb. 14, 2017

(54) MODIFIED RELEASE COMPOSITIONS OF EPALRESTAT OR A DERIVATIVE THEREOF AND METHODS FOR USING THE SAME

(75) Inventors: Isabel Kalofonos, Cambridge, MA (US); Judy Caron, Cambridge, MA (US); William Martin-Doyle, Cambridge, MA (US)

(73) Assignee: Bionevia Pharmaceuticals Inc., Cambridge, MA (US)

( * ) Notice: Subject to any disclaimer, the term of this patent is extended or adjusted under 35 U.S.C. 154(b) by 0 days.

(21) Appl. No.: 13/980,744

(22) PCT Filed: Jan. 20, 2012

(86) PCT No.: PCT/US2012/022094
§ 371 (c)(1),
(2), (4) Date: Mar. 12, 2014

(87) PCT Pub. No.: WO2012/100208
PCT Pub. Date: Jul. 26, 2012

(65) Prior Publication Data
US 2014/0296309 A1     Oct. 2, 2014

Related U.S. Application Data

(60) Provisional application No. 61/434,637, filed on Jan. 20, 2011.

(51) Int. Cl.
| | | |
|---|---|---|
| A61K 31/425 | (2006.01) | |
| A01N 43/78 | (2006.01) | |
| A61K 31/426 | (2006.01) | |
| A61K 9/20 | (2006.01) | |
| A61K 9/28 | (2006.01) | |
| A61K 47/26 | (2006.01) | |
| A61K 9/16 | (2006.01) | |
| A61K 9/00 | (2006.01) | |

(52) U.S. Cl.
CPC ........... *A61K 31/426* (2013.01); *A61K 9/1652* (2013.01); *A61K 9/2018* (2013.01); *A61K 9/2027* (2013.01); *A61K 9/2054* (2013.01); *A61K 9/2077* (2013.01); *A61K 9/282* (2013.01); *A61K 9/284* (2013.01); *A61K 9/2886* (2013.01); *A61K 47/26* (2013.01); *A61K 9/0019* (2013.01); *A61K 9/1623* (2013.01)

(58) Field of Classification Search
CPC .... A61K 31/426; A61K 47/26; A61K 9/1623; A61K 9/1652; A61K 9/2018; A61K 9/2027; A61K 9/2054; A61K 9/2077; A61K 9/282; A61K 9/284; A61K 9/2886
USPC ........................................................ 514/369
See application file for complete search history.

(56) References Cited

U.S. PATENT DOCUMENTS

| | | |
|---|---|---|
| 2,990,332 A | 6/1961 | Keating |
| 2,996,431 A | 8/1961 | Barry |
| 3,138,525 A | 6/1964 | Koff |
| 3,492,397 A | 1/1970 | Peters et al. |
| 3,499,960 A | 3/1970 | Macek et al. |
| 3,536,809 A | 10/1970 | Applezweig |
| 3,594,470 A | 7/1971 | Borodkin et al. |
| 3,598,123 A | 8/1971 | Zaffaroni |
| 3,835,221 A | 9/1974 | Fulberth et al. |
| 3,845,770 A | 11/1974 | Theeuwes et al. |
| 3,870,790 A | 3/1975 | Lowey et al. |
| 3,916,899 A | 11/1975 | Theeuwes et al. |
| 4,008,719 A | 2/1977 | Theeuwes et al. |
| 4,111,202 A | 9/1978 | Theeuwes |
| 4,138,475 A | 2/1979 | McAinsh et al. |
| 4,140,755 A | 2/1979 | Sheth et al. |
| 4,167,588 A | 9/1979 | Willard |
| 4,226,849 A | 10/1980 | Schor |
| 4,259,314 A | 3/1981 | Lowey |
| 4,327,725 A | 5/1982 | Cortese et al. |
| 4,357,469 A | 11/1982 | Schor |
| 4,369,172 A | 1/1983 | Schor et al. |
| 4,389,393 A | 6/1983 | Schor et al. |
| 4,415,547 A | 11/1983 | Yu et al. |
| 4,540,566 A | 9/1985 | Davis et al. |
| 4,612,008 A | 9/1986 | Wong et al. |
| 4,765,989 A | 8/1988 | Wong et al. |
| 4,783,337 A | 11/1988 | Wong et al. |
| 4,831,045 A * | 5/1989 | Tanouchi ............ C07D 277/20 514/342 |
| 4,839,177 A | 6/1989 | Colombo et al. |
| 4,871,548 A | 10/1989 | Edgren et al. |
| 4,894,239 A | 1/1990 | Nonomura et al. |
| 4,894,240 A | 1/1990 | Geoghegan et al. |

(Continued)

FOREIGN PATENT DOCUMENTS

| | | |
|---|---|---|
| EP | 0749751 A2 | 12/1996 |
| EP | 1106210 A2 | 6/2001 |

(Continued)

OTHER PUBLICATIONS

Berge et al., "Pharmaceutical salts." Journal of Pharmaceutical Sciences (1977); 66.1: 1-19.
Bundgaard et al., "Prodrugs of peptides IV: Bioreversible derivatization of the pyroglutamyl group by N-acylation and N-aminomethylation to effect protection against pyroglutamyl aminopeptidase." Journal of Pharmaceutical Sciences (1989); 78.2: 122-126. (Abstract Only).
Extended European Search Report for European Application No. 12736674.8, mailed Jun. 12, 2014, 6 pages.
Extended European Search Report for European Application No. 15184332.3, mailed May 23, 2016, 7 pages.
Fujioka et al., "Glycemic control in patients with type 2 diabetes mellitus switched from twice-daily immediate-release metformin to a once-daily extended-release formulation." Clinical Therapeutics (2003); 25.2: 515-529. (Abstract Only).

(Continued)

*Primary Examiner* — My-Chau T Tran
(74) *Attorney, Agent, or Firm* — Cooley LLP

(57) ABSTRACT

Modified release pharmaceutical compositions of epalrestat are provided. Methods of manufacturing the tablets and treating various diseases and conditions, including diabetes and diabetic complications, by administering the modified release compositions to patients in need thereof are also provided.

21 Claims, 5 Drawing Sheets

(56) References Cited

U.S. PATENT DOCUMENTS

| | | | |
|---|---|---|---|
| 5,059,595 A | 10/1991 | Le Grazie | |
| 5,073,543 A | 12/1991 | Marshall et al. | |
| 5,082,668 A | 1/1992 | Wong et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,674,533 A | 10/1997 | Santus et al. | |
| 5,733,566 A | 3/1998 | Lewis | |
| 5,811,126 A | 9/1998 | Krishnamurthy | |
| 6,403,120 B1 | 6/2002 | Sherman et al. | |
| 6,419,958 B2 | 7/2002 | Sherman et al. | |
| 6,919,373 B1 | 7/2005 | Lam et al. | |
| 7,101,912 B2 | 9/2006 | Xiang et al. | |
| 2005/0181041 A1 | 8/2005 | Goldman | |
| 2006/0058310 A1 | 3/2006 | Takenobu et al. | |
| 2006/0280794 A1* | 12/2006 | Hamaguchi | A61K 9/209 424/472 |
| 2009/0098202 A1 | 4/2009 | Friedl et al. | |
| 2009/0220611 A1* | 9/2009 | Dargelas | A61K 9/5073 424/495 |
| 2009/0270490 A1 | 10/2009 | Srivastava et al. | |
| 2010/0203129 A1 | 8/2010 | Andersen et al. | |
| 2010/0305208 A1 | 12/2010 | Dudhara et al. | |
| 2011/0136772 A1* | 6/2011 | Clark | A61K 9/2054 514/178 |
| 2012/0328675 A1* | 12/2012 | Awamura | A61K 31/045 424/400 |

FOREIGN PATENT DOCUMENTS

| | | | |
|---|---|---|---|
| JP | 2004-210703 A | | 7/2004 |
| JP | 2005139085 A | * | 6/2005 |
| JP | 2005-298424 A | | 10/2005 |
| JP | 2007-099680 A | | 4/2007 |
| WO | WO 99/26659 A1 | | 6/1999 |
| WO | WO 02/00196 A2 | | 1/2002 |
| WO | WO 2004/016251 A1 | | 2/2004 |
| WO | WO 2004/108067 A2 | | 12/2004 |
| WO | WO 2010/011922 A2 | | 1/2010 |
| WO | WO 2010/011926 A2 | | 1/2010 |
| WO | WO 2010/028132 A2 | | 3/2010 |

OTHER PUBLICATIONS

Guidance for Industry SUPAC-MR: Modified Release Solid Oral Dosage Forms, Sep. 1997, [on-line] [Found on Apr. 27, 2015] found in the Internet at <URL: http://www.fda.gov/downloads/Drugs/Guidances/ucm070640.pdf>), 52 pages.

International Preliminary Report on Patentability for International Application No. PCT/US2012/022094, mailed Jul. 23, 2013, 7 pages.

International Search Report and Written Opinion for International Application No. PCT/US2012/022094, mailed May 4, 2012, 9 pages.

Lawson-Yuen et al., "The use of betaine in the treatment of elevated homocysteine." Molecular Genetics and Metabolism (2006); 88.3: 201-207.

Lebo et al., "Multicolor in situ hybridization and linkage analysis order Charcot-Marie-Tooth type I (CMTIA) gene-region markers." American Journal of Human Genetics (1992); 50.1: 42.

Shi et al., "Impact of dose frequency on compliance and health outcomes: a literature review (1966-2006)." Expert Review of Pharmacoeconomics & Outcomes Research (2007); 7.2: 187-202. (Abstract Only).

Swinnen et al., "A 24-week, randomized, treat-to-target trial comparing initiation of insulin glargine once-daily with insulin detemir twice-daily in patients with type 2 diabetes inadequately controlled on oral glucose-lowering drugs." Diabetes Care (2010); 33.6: 1176-1178.

Wijekoon et al., "Homocysteine metabolism in ZDF (type 2) diabetic rats." Diabetes (2005); 54.11: 3245-3251.

* cited by examiner

MODIFIED RELEASE COMPOSITIONS OF EPALRESTAT OR A DERIVATIVE THEREOF AND METHODS FOR USING THE SAME

CROSS REFERENCE TO RELATED APPLICATION

This application is a U.S. national stage application of International Application No. PCT/US2012/022094, which was filed on Jan. 20, 2012 and claims priority from U.S. Provisional Application Ser. No. 61/434,637, filed Jan. 20, 2011, which is hereby incorporated by reference in its entirety for all purposes.

FIELD OF THE INVENTION

The present invention relates to novel modified release pharmaceutical compositions of epalrestat and methods of treating various diseases and conditions, including diabetes and diabetic complications, by administering the compositions to patients in need thereof.

BACKGROUND OF THE INVENTION

Epalrestat, (5-[(1Z,2E)-2-methyl-3-phenylpropenylidene]-4-oxo-2-thioxo-3-thiazolidineacetic acid), shown below, is an aldose reductase inhibitor. The preparation and pharmacologic activity of epalrestat is described in U.S. Pat. No. 4,831,045. Epalrestat has previously been described as useful for treating various conditions, including diabetes and diabetic complications, as well as affording cardioprotection in non-diabetic patients.

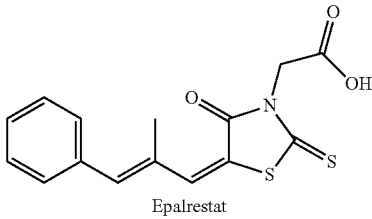 [SMILES: CC(=C\c1ccccc1)/C=C1/SC(=S)N(CC(=O)O)C1=O]

Epalrestat

Epalrestat has a positive indication for the treatment of diabetic neuropathy, and has been reported as useful for the treatment of other diabetic complications including, for example, diabetic retinopathy, diabetic nephropathy, diabetic cardiomyopathy, diabetic gastroparesis, diabetic microangiopathy, and diabetic macroangiopathy in mammals.

Epalrestat is also useful in affording cardioprotection to subjects who may not be suffering from diabetes, and as a neuroprotectant or treatment for neurological or neurodegenerative disorders. Therapeutic activity of epalrestat in various conditions has been demonstrated in the clinical literature. For example, see Machii H. et al. (1996). *Gendai Iryo*, v. 28, p. 1273; Miyamoto S. et al. (1986). *Gendai Iryo*, v. 18 (Extra Issue HI), p. 82; Goto Y. et al. (1990). *Journal of Clinical and Experimental Medicine*, v. 152, p. 405; Nakano K. et al. (1990). *Journal of Clinical and Experimental Medicine*, v. 152, p. 137; Okamoto H. et al. (2003). *Internal Medicine*, v. 42, pp. 655-664; Hamada Y. et al. (2000). *Diabetes Care*, v. 23, pp. 1539-44.; Goto Y. et al. (1993). *Diabet Med*, v. 10(suppl 2), pp. S39-43; Goto Y. et al. (1995). *Biomed Pharmacother*, v. 49, pp. 269-277; Uchida K. et al. (1995). *Clin Ther*, v. 17, pp. 460-466; Hotta N. et al. (1996). *J Diabetes Complications*, v. 10, pp. 168-172; Hotta N. et al. (2006). *Diabetes Care*, v. 29, pp. 1538-1544; Matsuoka K. et al. (2007). *Diabetes Res Clin Pract*, v. 77(suppl 1), pp. S263-268; Nakayama M. et al. (2001). *Diabetes Care*, v. 24, pp. 1093-1098; Baba M. (2003). *Journal of the Peripheral Nervous System*, v. 8, p. 170; Yasuda H. et al. (2000). *Diabetes Care*, v. 23, p. 705; IkedaT et al. (1999). *Diabetes Research and Clinical Practice*, v. 43, pp. 193-198; Katayama M. et al. (1995). *Electroencephalography and Clinical Neurophysiology/Electromyography and Motor Control*, v. 97, p. 81; and Misawa S. et al. (1996). *Neurology*, v. 66, pp. 1545-1549.

SUMMARY OF THE INVENTION

Currently, epalrestat is prescribed as an immediate release formulation, and therefore must be administered three times a day.

In order to provide for an effective once-a-day form of epalrestat, there is a need for unique formulation approaches that provide the desired therapeutic effects while minimizing, if not eliminating, undesired side effects. Accordingly, in one embodiment, the modified release epalrestat composition of the invention provides a minimum blood epalrestat concentration ($C_{min}$) at steady state above the minimum therapeutically effective blood concentration. In another embodiment, the modified release epalrestat composition provides a maximum blood epalrestat concentration ($C_{max}$) at steady state below the maximum toxic blood concentration over the treatment period.

Described herein is a pharmaceutical composition comprising a modified release formulation of epalrestat or a pharmaceutically acceptable derivative thereof, which maintains an adequate epalrestat plasma concentration-time profile to effectively treat a patient in need thereof, using once-a-day administration.

In one embodiment of the invention, a modified release pharmaceutical composition comprising epalrestat or a pharmaceutically acceptable derivative thereof, and a pharmaceutically acceptable excipient, is provided. The modified release composition, in one embodiment, is a sustained release, controlled release, bi-modal release or delayed release composition. In one embodiment, the epalrestat is selected from epalrestat isomer 1, epalrestat isomer 2, epalrestat isomer 3 or epalrestat isomer 4. In one embodiment, the modified release epalrestat pharmaceutical composition comprises a pharmaceutically acceptable epalrestat derivative. In a further embodiment, the derivative is choline hydrogen diepalrestat or betaine hydrogen diepalrestat.

In another embodiment of the invention, a modified release pharmaceutical composition of epalrestat is provided. In this embodiment, the modified release pharmaceutical composition provides the same or substantially the same epalrestat bioavailability, or at least about 70% epalrestat bioavailability, or at least about 75% epalrestat bioavailability, or at least about 80% epalrestat bioavailability, or at least about 85% epalrestat bioavailability compared to the epalrestat bioavailability obtained from an immediate release composition. In a further embodiment, the pharmaceutical composition comprises a crystalline salt of epalrestat. In yet a further embodiment, the crystalline salt is a potassium anhydrate salt, a sodium andydrate salt or a 1-(2-hydroxyethyl)-pyrrolidine andydrate salt.

Yet another embodiment of the invention is directed to a method for treating diabetes or a diabetic complication in a subject in need thereof. The method comprises administering to the subject a modified release pharmaceutical composition comprising epalrestat or a pharmaceutically acceptable derivative thereof, and a pharmaceutically acceptable excipient. In a further embodiment, the subject is administered the composition once daily, twice weekly, three times per week or four times per week. In one embodiment, the diabetic complication is selected from the group consisting of diabetic neuropathy, diabetic nephropathy, diabetic cardiomyopathy, diabetic retinopathy, diabetic gastroparesis, cataracts, foot ulcers, diabetic macroangiopathy, diabetic microangiopathy, high blood glucose and high HbAlc levels.

Another embodiment of the invention is directed to a method for inhibiting aldose reductase in a subject in need thereof. The method comprises administering to the subject a modified release pharmaceutical composition comprising epalrestat or a pharmaceutically acceptable derivative thereof, and a pharmaceutically acceptable excipient. In a further embodiment, the subject is administered the composition once daily, twice weekly, three times per week or four times per week. In one embodiment, the pharmaceutical composition administered to the subject in need thereof comprises epalrestat isomer 1, for example, choline hydrogen diepalrestat. In another embodiment, the pharmaceutical composition comprises a crystalline salt of epalrestat. In a further embodiment, the crystalline salt is a potassium anhydrate salt, a sodium andydrate salt or a 1-(2-hydroxyethyl)-pyrrolidine andydrate salt.

A method is also provided herein for treating cardiac tissue ischemia in a subject in need thereof. The method comprises administering to the subject a modified release pharmaceutical composition comprising epalrestat or a pharmaceutically acceptable derivative thereof, and a pharmaceutically acceptable carrier. In one embodiment, the modified release composition is a sustained release, delayed release, bi-modal release or controlled release composition. In one embodiment, the pharmaceutical composition administered to the subject in need thereof comprises diepalrestat, epalrestat isomer 1, for example, choline hydrogen diepalrestat. In another embodiment, the pharmaceutical composition administered to the subject in need thereof comprises a crystalline salt of epalrestat. In a further embodiment, the crystalline salt is a potassium anhydrate salt, a sodium andydrate salt or a 1-(2-hydroxyethyl)-pyrrolidine andydrate salt.

DETAILED DESCRIPTION OF THE INVENTION

Definitions

Figure 1:
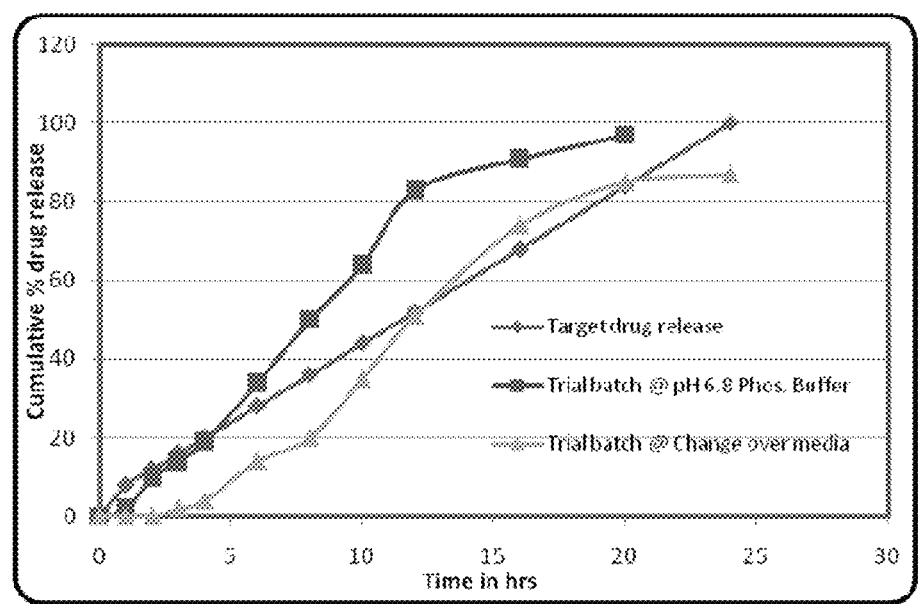
FIG. 1 is a graph showing the dissolution of a tablet of the present invention compared to a 24. hr. target release profile.

"Epalrestat" refers to the aldose reductase inhibitor having the molecular formula $C_{15}H_{13}NO_3S_2$ and the IUPAC name of 2-[5-[3-cyclohexyl-2-methylprop-2-enylidene]-4-oxo-2-thioxo-3-thiazolidinyl]acetic acid. Unless otherwise indicated, epalrestat refers to one of the isomers of epalrestat referred to herein, or a combination thereof. Additionally, diepalrestat, an "epalrestat derivative" and a "pharmaceutically acceptable epalrestat derivative" are also encompassed by the term "epalrestat."

A pharmaceutically acceptable epalrestat derivative encompasses cocrystals, salts, free acids, prodrugs (e.g., esters), polymorphs, and solvates of epalrestat. It should be understood by one of ordinary skill in the art that the various forms of the pharmaceutically acceptable epalrestat derivative do not exclude each other. That is, a pharmaceutically acceptable epalrestat derivative can be in two or more forms simultaneously. For example, a pharmaceutically acceptable epalrestat salt and/or prodrug may also exist in a solvate form. Crystalline epalrestat salts, solvates, prodrugs, and combinations thereof are pharmaceutically acceptable epalrestat derivatives.

An "isomer" of compound X, as used herein, refers to a compound with the same molecular formula as compound X, having a different structural formula. "Stereoisomers" have the same bond structure, but different geometrical positioning of atoms and/or functional groups.

"Cis-trans isomerism" is a form of stereoisomerism describing the orientation of atoms and/or functional groups around a double bond. A "cis" isomer means the atoms and/or functional groups are on the same side of the double bond, while a "trans" isomer has the atoms and/or double bonds on opposite sides of the double bond. The cis/trans system for naming isomers is not effective when there are more than two different substituents on a double bond, and therefore, the E/Z notation is used. Z (from the German zusammen) means together and corresponds to the term cis; while E (from the German entgegen) means opposite, and corresponds to the term trans.

The phrase "pharmaceutically acceptable" refers to molecular entities and compositions that are generally regarded as safe. In particular, pharmaceutically acceptable carriers used in the practice of this invention are physiologically tolerable and do not typically produce an allergic or similar unfavorable reaction (for example, gastric upset, dizziness) when administered to a subject. Preferably, as used herein, the term "pharmaceutically acceptable" means approved by a regulatory agency of the appropriate governmental agency or listed in the U.S. Pharmacopoeia or other generally recognized pharmacopoeia for use in animals, and more particularly in humans.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

The term "treating" includes: (1) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (2) inhibiting the state, disorder or condition (i.e., arresting, reducing or delaying the development of the disease, or a relapse thereof in case of maintenance treatment, of at least one clinical or subclinical symptom thereof); and/or (3) relieving the condition (i.e., causing regression of the state, disorder or condition or at least one of its clinical or subclinical symptoms). The benefit to a subject to be treated is either statistically significant or at least perceptible to the subject or to the physician.

A "neurological disorder" as used herein means an aberration from clinically normal neural cell activity (i.e., compromised neural cell activity) and includes, by way of example only, neurodegenerative disease (of the CNS and/or PNS), neuropathies associated with toxicity (neurotoxicity) such as chemotherapy (i.e., vincristine or cisplatin-induced motor neuropathy) and alcohol consumption, immune-mediated neurodiseases such as multiple sclerosis (MS) and Guillain-Barre syndrome, hereditary neuropathies such as Charcot-Marie-Tooth neuropathies (see Lebo et al. (1992) *Am. J. Hum. Genet.*, v. 50, pp. 42-55), injury due to trauma, and compromised function due to senescence.

"Effective amount" means an amount of epalrestat in a modified release composition of the present invention sufficient to result in the desired therapeutic response. The therapeutic response can be any response that a user or clinician will recognize as an effective response to the therapy. It is further within the skill of one of ordinary skill in the art to determine an appropriate treatment duration, appropriate doses, and any potential combination treatments, based upon an evaluation of therapeutic response.

The term "subject" includes humans and other mammals, such as domestic animals (e.g., dogs and cats).

The term "salts" can include acid addition salts or addition salts of free bases. Suitable pharmaceutically acceptable salts (for example, of the carboxyl terminus of the amino acid or peptide) include, but are not limited to, metal salts such as sodium, potassium and cesium salts, for example sodium or potassium andydrate salts; alkaline earth metal salts such as calcium and magnesium salts; organic amine salts such as triethylamine, guanidine and N-substituted guanidine salts, acetamidine and N-substituted acetamidine, pyridine, pyrrolidine, picoline, ethanolamine, triethanolamine, dicyclohexylamine, and N,N'-dibenzylethylenediamine salts. Pharmaceutically acceptable salts (of basic nitrogen centers) include, but are not limited to inorganic acid salts such as the hydrochloride, hydrobromide, sulfate, phosphate; organic acid salts such as trifluoroacetate and maleate salts; sulfonates such as methanesulfonate, ethanesulfonate, benzenesulfonate, p-toluenesulfonate, camphor sulfonate and naphthalenesulfonate; and amino acid salts such as arginate, gluconate, galacturonate, alaninate, asparginate and glutamate salts (see, for example, Berge, et al. (1977). "Pharmaceutical Salts," *J. Pharma. Sci.*, v. 66, p. 1).

As used herein, "solvate" means a complex formed by solvation (the combination of solvent molecules with molecules or ions of the active agent of the present invention), or an aggregate that consists of a solute ion or molecule (the active agent of the present invention) with one or more solvent molecules. In one embodiment, the solvate is a hydrate. Examples of hydrate include, but are not limited to, hemihydrate, monohydrate, dihydrate, trihydrate, hexahydrate, etc. The solvate/hydrate is typically formed via hydration which is either part of the preparation of the present compound or through natural absorption of moisture by the anhydrous compound of the present invention.

The term "prodrug" refers to a precursor of a pharmaceutically active compound wherein the precursor itself may or may not be pharmaceutically active but, upon administration, will be converted, either metabolically or otherwise, into the pharmaceutically active compound or drug of interest. For example, prodrug can be an ester or an ether form of a pharmaceutically active compound. Various types of prodrug have been prepared and disclosed for a variety of pharmaceuticals. See, for example, Bundgaard, H. and Moss, J. (1989). *J. Pharm. Sci.*, v. 78, pp. 122-126. Thus, one of ordinary skill in the art knows how to prepare these prodrugs with commonly employed techniques of organic synthesis.

The term "ester" means any ester of a present compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The hydrolysable esters of the present compounds are the compounds whose carboxyls are present in the form of hydrolysable ester groups. That is, these esters are pharmaceutically acceptable and can be hydrolyzed to the corresponding carboxyl acid in vivo. These esters may be conventional ones, including lower alkanoyloxyalkyl esters, e.g., pivaloyloxymethyl and 1-pivaloyloxyethyl esters; lower alkoxycarbonylalkyl esters, e.g., methoxycarbonyloxymethyl, 1-ethoxycarbonyloxyethyl, and 1-isopropylcarbonyloxyethyl esters; lower alkoxymethyl esters, e.g., methoxymethyl esters, lactonyl esters, benzofuran keto esters, thiobenzofuran keto esters; lower alkanoylaminomethyl esters, e.g., acetylaminomethyl esters. Other esters can also be used, such as benzyl esters and cyano methyl esters. Other examples of these esters include: (2,2-dimethyl-1-oxypropyloxy)methyl esters; (1RS)-1-acetoxyethyl esters, 2-[(2-methylpropyloxy)carbonyl]-2-pentenyl esters, 1-[[(1-methylethoxy)carbonyl]-oxy]ethyl esters; isopropyloxycarbonyloxyethyl esters, (5-methyl-2-oxo-1,3-dioxole-4-yl) methyl esters, 1-[[(cyclohexyloxy)carbonyl]oxy]ethyl esters; 3,3-dimethyl-2-oxobutyl esters. It is obvious to those skilled in the art that hydrolysable esters of the compounds of the present invention can be formed at free carboxyls of said compounds by using conventional methods. Esters include pivaloyloxymethyl esters, isopropyloxycarbonyloxyethyl esters and (5-methyl-2-oxo-1,3-dioxole-4-yl) methyl esters.

The term "active ingredient," or "active pharmaceutical ingredient," unless specifically indicated, is to be understood as referring to the epalrestat portion of the modified release formulation, described herein.

Compositions of the Invention

The present invention is directed to novel modified release pharmaceutical compositions of epalrestat or epalrestat derivatives, or a combination thereof. A "modified release pharmaceutical composition," as used herein, refers to a type of pharmaceutical composition in which the active pharmaceutical ingredient ("API," i.e., epalrestat or epalrestat derivative) is not released immediately. Therefore, a modified release epalrestat pharmaceutical composition can be administered less frequently than an immediate release epalrestat composition. However, the modified release composition still achieves the pharmacokinetics necessary to treat the indications and diseases treatable by the immediate release formulation counterpart. For example, in one embodiment, the modified release composition of the invention releases epalrestat over a 15 hr. time period, or an 18 hr. time period, or a 24 hr. time period.

Sustained, delayed, extended, bi-modal release and controlled release compositions are each encompassed by the term "modified release." A controlled release pharmaceutical composition is characterized by zero-order release (i.e., the epalrestat or epalrestat derivative is released over time irrespective of concentration). Sustained release pharmaceutical compositions are characterized by slow release of epalrestat or the epalrestat derivative over some time period. A sustained release composition may or may not be a controlled-release composition. Delayed release compositions are characterized by a time lag between administration of the composition, and release of the API (i.e., epalrestat or epalrestat derivative) from the composition. Extended release compositions allow for a greater reduction in the frequency of administration of the API, as compared to conventional release (i.e., immediate release) compositions.

An improved epalrestat formulation with prolonged duration of action that achieves prolonged, stable plasma concentrations, and with decreased frequency of administration is provided herein. Once daily administration of epalrestat or its derivatives is advantageous over the three-times-a-day administration in terms of both patient compliance and reduced adverse events, thus providing better treatment of the conditions for which epalrestat or its derivatives is indicated.

A reduced frequency of daily administration of a particular medication has been associated with improved clinical outcomes in patients with diabetes and numerous other conditions, as described in the art. For example, see, Shi L et al. (2007). *Expert Review of Pharmacoeconomics & Outcomes Research*, v. 7, pp. 187-202; Fukioka K, et al. (2003). Clinical Therapeutics, v. 25, pp. 515-529; and Schernthaner G. (2010). *Diabetic Medicine*, v. 7, pp. 739-743. Once-a-day administration of epalrestat or its derivatives may therefore result in improved clinical outcomes in patients receiving the medication, due to positive effects on medication adherence by patients.

In one embodiment, the modified release epalrestat composition of the invention provides the same or substantially the same epalrestat bioavailability (i.e., area under the plasma concentration-time curve) as the epalrestat bioavailability provided by an immediate release epalrestat composition. In a further embodiment, the time to $C_{max}$ (i.e., $t_{max}$) for the modified release composition is prolonged, as compared to an immediate release composition. In yet a further embodiment, the time to $C_{max}$ (i.e., $t_{max}$) for the modified release composition is prolonged by about 1 hr., about 2 hr., about 3 hr., about 4 hr., about 5 hr., about 6, hr. or about 7 hr., compared to an immediate release epalrestat composition.

In another embodiment, the modified release epalrestat composition of the invention provides at least about 60%, at least about 65%, at least about 70%, at least about 75%, at least about 80%, at least about 85%, at least about 90% or at least about 95% the epalrestat bioavailability (i.e., area under the plasma concentration-time curve) as the epalrestat bioavailability provided by an immediate release epalrestat composition.

As stated above, in one embodiment, the present invention provides modified release pharmaceutical compositions of epalrestat. When epalrestat is administered as an immediate release 50 mg dosage to health adult volunteers, the pharmacokinetic parameters include a $C_{max}$ of 3.9 µg/mL at a $t_{max}$ of 1.05 hours, a $t_{1/2}$ of 1.8 hours, and a total $AUC_{0-\infty}$ of 6.4 µg/mL·hour. Plasma levels of epalrestat fall quickly after administration of 50 mg tablets of epalrestat free acid, and reach 0.37 µg/mL 4 hours after administration (Machii H. et al. Gendai Iryo 1996; 28:1273). In one embodiment, the modified release epalrestat compositions provided herein provide a $C_{max}$ the same or substantially the same as an immediate release epalrestat composition. In another embodiment, a modified release epalrestat composition of the present invention provides a $C_{max}$ that is at least 70%, at least 75%, at least 80%, at least 85%, at least 90%, at least 100%, at least 110%, or at least 120% of the $C_{max}$ provided by an immediate release epalrestat composition.

The modified release epalrestat composition provided herein is suitable for once-a-day administration, such that once-a-day administration of the pharmaceutical composition provides steady state blood levels of epalrestat that are comparable to steady state plasma concentrations of epalrestat achieved with three times daily administration of 50 mg immediate release epalrestat free acid tablets. The composition provided herein can include epalrestat, or an epalrestat derivative.

Although in one embodiment, the modified release epalrestat composition is administered once-daily, the invention is not limited thereto. For example, the composition can be administered two times per day, once daily, two times per week, three times per week, four times per week, five times per week or six times per week. It is within the ordinary skill in the art to optimize dosing regimens.

In one embodiment, the modified release composition is formulated for once-a-day administration of epalrestat (or a derivative thereof). In this embodiment, the pharmaceutical composition provides steady state blood levels of epalrestat that are comparable to steady state plasma concentrations of epalrestat achieved with three times daily administration of 50 mg immediate release epalrestat free acid tablets, for example 50 mg Kinedak tablets (Ono Pharmaceuticals, Japan).

In another embodiment, the modified release composition of the present invention achieves epalrestat plasma concentrations comparable to steady state plasma concentrations achieved with three times a day dosing of from about 10 to about 200 mg immediate release epalrestat free acid tablets, for example 25 mg, 50 mg or 100 mg tablets.

In one embodiment, once-a-day administration of the modified, e.g., controlled release pharmaceutical composition of the invention provides steady state blood levels of epalrestat in the range of about 0.1 µg/mL to about 15.0 µg/mL, for example about 0.5 µg/mL to about 12.0 µg/mL, or about 1 µg/mL to about 10.0 µg/mL. In another embodiment, once-a-day administration of the modified release epalrestat composition provides steady state blood $C_{max}$ levels of epalrestat in the range of about 1.0 µg/mL to about 15.0 µg/mL and $C_{min}$ levels of epalrestat in the range of about 0.1 µg/mL to about 0.5 µg/mL, or about 0.1 µg/mL to about 1.0 µg/mL. In yet another embodiment, once-a-day administration of the controlled release pharmaceutical composition provides steady state areas under the curve (AUCs) in the range of about 2 to about 80 µg/mL·hour, e.g., about 2 to 70 µg/mL·hour, about 2 to 60 µg/mL·hour, about 2 to 50 µg/mL·hour, about 2 to 40 µg/mL·hour, about 2 to 30 µg/mL·hour, about 10 to 80 µg/mL·hour, about 20 to 80 µg/mL·hour, about 30 to 80 µg/mL·hour, about 40 to 80 µg/mL·hour, about 50 to 80 µg/mL·hour.

In one embodiment, the modified release epalrestat composition provided herein exhibits a drug release profile substantially corresponding to the following pattern: after 2 hours, no more than about 40% of the total active is released; after 4 hours, from about 40-65% of the total active is released; after 8 hours, from about 60-85% of the total active is released; and after 12 hours, from about 75-90% of the total active is released. The disclosed dosage form provides therapeutically effective epalrestat plasma concentration over a period of at least 24 hours, for example, 24 hours, to treat a patient in need thereof. In another embodiment, the modified release epalrestat composition exhibits a drug release profile substantially corresponding to the target profiles given in FIGS. 1-5.

In another embodiment, the modified release epalrestat composition provided herein exhibits a drug release profile substantially corresponding to the following pattern: after 2 hours, no more than about 30% of the total active is released; after 4 hours, from about 30-55% of the total active is released; after 8 hours, from about 45-75% of the total active is released; and after 12 hours, from about 60-95% of the total active is released. The disclosed dosage form provides therapeutically effective epalrestat plasma concentration over a period of at least 24 hours, for example, 24 hours, to treat a patient in need thereof.

Epalrestat or a pharmaceutically acceptable derivative may be administered as crystalline or amorphous products in the modified release compositions. Epalrestat or the pharmaceutically acceptable derivative may be obtained, for example, as solid plugs, powders, or films by methods such as precipitation, crystallization, freeze drying, or spray drying, or evaporative drying. Microwave or radio frequency drying may be used for this purpose.

Isomers of Epalrestat

The present invention can employ one or more isomers of epalrestat in the modified release formulation. Because epalrestat has two double bonds in its carbon backbone, four stereoisomers are possible, as set forth below. Each of the stereoisomers (or a combination of two or more isomers) can be used in the modified release compositions of the present invention.

Isomer 1: 5-[(1Z,2E)-2-methyl-3-phenylpropenylidene]-4-oxo-2-thioxo-3-thiazolidineacetic acid;
Isomer 2: 5-[(1Z,2Z)-2-methyl-3-phenylpropenylidene]-4-oxo-2-thioxo-3-thiazolidineacetic acid;
Isomer 3: 5-[(1E,2E)-2-methyl-3-phenylpropenylidene]-4-oxo-2-thioxo-3-thiazolidineacetic acid; and
Isomer 4: 5-[(1E,2Z)-2-methyl-3-phenylpropenylidene]-4-oxo-2-thioxo-3-thiazolidineacetic acid).

In one embodiment of the invention, the modified release composition of epalrestat comprises isomer 1 of epalrestat. In another embodiment of the invention, the modified release composition of epalrestat comprises isomer 2 of epalrestat. In yet another embodiment of the invention, the modified release composition of epalrestat comprises isomer 3 of epalrestat. In one embodiment of the invention, the modified release composition of epalrestat comprises isomer 4 of epalrestat.

The modified release composition of the present invention may comprise one isomer, or a combination of isomers. For example, in one embodiment, a modified release formulation of the present invention comprises isomer 1 and isomer 2 of epalrestat, or isomers 1 and 3 of epalrestat, or isomers 1 and 4, or isomers 2 and 3, or isomers 2 and 4, or isomers 3 and 4. In yet another embodiment, a combination of three isomers, or a combination of all four isomers, is employed in the modified release epalrestat composition.

Additionally, one or more crystal forms of epalrestat can be present in a composition. For example, in one embodiment, the modified release composition comprises isomer 1 of epalrestat, present as a choline hydrogen diepalrestat cocrystal (also referred to herein as "choline hydrogen diepalrestat" and "choline hydrogen diaced cocrystal of epalrestat"). In this embodiment, the cocrystal of isomer 1 is complexed with choline in a 2:1 molecular ratio (see WO 2010/028132). Other crystal forms of epalrestat amenable for use with the modified release compositions of the present invention are disclosed in WO 2010/011926 (betaine cocrystal of epalrestat) and WO 2010/011922 (crystalline salts of epalrestat). Each of these PCT publications is incorporated herein by reference in their entirety. Each of the isomers of epalrestat can be present in a cocrystal, and multiple distinct cocrystals can be present in a modified release epalrestat composition of the invention.

Crystalline salts of epalrestat may also be used in the compositions and methods of the invention. In one embodiment, one or more of the crystalline salts disclosed in WO 2010/011922 is used in a modified release epalrestat composition of the present invention. For example, a potassium anhydrate salt, a sodium anhydrate salt, and a 1-(2-hydroxyethyl)-pyrrolidine anhydrate salt are all within the scope of the present invention.

Modified Release Formulations

Numerous techniques exist in the prior art for preparing modified, sustained or controlled release pharmaceutical formulations. Controlled release means or delivery devices that are well known to those of ordinary skill in the art, are described, for example in U.S. Pat. Nos. 3,845,770; 3,916,899; 3,536,809; 3,598,123; 4,008,719; 5,674,533; 5,059,595; 5,591,767; 5,120,548; 5,073,543; 5,354,556; 5,733,566 and 6,403,120, the disclosures of which are incorporated herein by reference in their entireties. Each of these techniques is useful for achieving an epalrestat modified release composition.

The composition may be formulated to various delivery systems including matrix delivery systems (U.S. Pat. No. 4,871,548), osmotic delivery systems (U.S. Pat. No. 4,612,008), and mutiparticulate delivery systems (U.S. Pat. No. 4,894,240). Matrix delivery systems are known to the field of pharmaceutical drug delivery (U.S. Pat. Nos. 3,870,790; 4,140,755; 4,167,588; 4,226,849; 4,259,314; 4,357,469; 4,369,172; 4,389,393; 4,540,566 and 4,839,177, the disclosures of which are incorporated herein by reference in their entirety). The osmotic delivery systems have been reported in a number of patents (U.S. Pat. Nos. 4,111,202, 4,327,725, 4,612,008, 4,765,989; 4,783,337, 5,082,668, 6,919,373, the disclosures of which are incorporated herein by reference in their entirety). The multiparticulate delivery systems typically involve hard gelatin capsule or compressed tablets containing film-coated spheroids or beads, as described, for example, by U.S. Pat. Nos. 2,996,431, 3,492,397, 3,835,221, 4,138,475, 4,415,547, 4,894,240 and 6,419,958, the disclosures of which are incorporated herein by reference in their entirety. Use of ionic exchange resin for sustained release of a pharmaceutical agent has also been disclosed in U.S. Pat. Nos. 2,990,332, 3,138,525, 3,499,960, 3,594,470, and 4,894,239, the disclosures of which are incorporated herein by reference in their entirety. In addition, the controlled-release of prodrugs of carbidopa/L-dopa was disclosed in an U.S. Pat. No. 7,101,912 for treatment of Parkinson disease, the disclosures of which are incorporated herein by reference in their entirety.

In one embodiment, epalrestat or the epalrestat derivative is embedded in a matrix of one or more insoluble substances. Upon dissolution of the tablet, the epalrestat or epalrestat derivative is released through the matrix.

In another embodiment, a polymer-based tablet with a laser drilled hole on one side, and a porous membrane on the other side, is employed. When the pharmaceutical composition comes into contact with acids present in the gastrointestinal tract, the acids push through the porous membrane, which results in the drug being released through the laser-drilled hole. This type of tablet construction results in modified release of epalrestat.

Multi-Layered Pellets/Particles (Microencapsulation)

In one embodiment, the formulation of the present invention is comprised of pellets of epalrestat. The epalrestat pellets, in one embodiment, have consistent bulk density and low friability.

The epalrestat pellets, in one embodiment comprise an inert core comprising any of the commonly known pellet starting materials, for example, starch, sugar (e.g., sucrose), microcrystalline cellulose, glass, vegetable gums or waxes can be used as the starting material. The inert cores amenable for use with the invention do not react with epalrestat or a derivative thereof. In one embodiment, the inert cores are coated with epalrestat solution or suspension, and further coated with a polymer, as described further below. In another embodiment, the pellets contain multiple layers of epalrestat.

In order to increase the bioavailability of epalrestat, the epalrestat can be formulated into fine particulate or nanoparticules, before dissolving in solution or creating an epalrestat suspension. The epalrestat solution or suspension is then coated onto inert cores, as described below.

A suspension or solution of epalrestat, in one embodiment, is applied to the inert cores by spraying. The suspension or solution further comprises a binder or binding agent, in addition to epalrestat or the pharmaceutically acceptable derivative thereof. As provided above, the epalrestat formulations, in one embodiment, include one or more isomers of epalrestat, for example, two distinct stereoisomers.

The binder/binding agent, in one embodiment, is a film-forming polymer that possesses high adhesivity and an appropriate viscosity, to assure good adhesion between the inert cores and epalrestat solution. The binding agents employed can be any film-forming binding agent commonly known in the art. For example, in one embodiment, the binding agent is selected from cellulose ether (e.g., ethyl cellulose), polyoxide, polyacrylate, polyethylene, polypropylene, polyurethane, hydroxypropyl methylcellulose (HPMC), hydroxypropyl cellulose and polyvinylpyrrolidone (PVP). In a further embodiment, mixtures of two or more of the aforementioned binding agents are employed.

In one embodiment of the present invention, the binding agent is a water insoluble polymer such as ethylcellulose. In another embodiment of the invention, a film-forming water soluble binder may be combined with the water insoluble binder. In one embodiment, the film-forming water soluble binding agent is selected from polyvinylpyrrolidone (PVP) or hydroxypropyl methylcellulose (HPMC).

The epalrestat solution or suspension is applied to the inert cores using methods known to those of ordinary skill in the art. For example, fluidized bed coating, rotor granulation or pan coating techniques may all be employed to achieve the coated cores.

Once the cores are coated with the epalrestat solution or suspension, the coated cores (i.e., epalrestat pellets) are now "immediate release epalrestat pellets." The immediate release epalrestat pellets can be used in a modified release epalrestat composition, as discussed below, to provide distinct release profiles of epalrestat.

The immediate release epalrestat pellets, in one embodiment, are further coated with a water insoluble polymer layer to achieve extended release epalrestat pellets. The pellets can include one, two, three or four water insoluble layers. Without wishing to be bound by theory, the release of the drug is believed to be primarily controlled by the diffusion of the epalrestat or pharmaceutically acceptable derivative thereof through the polymer coating. However, degradation of the water insoluble layers may also contribute to the epalrestat modified release profile.

In one embodiment, both immediate release epalrestat pellets and extended release epalrestat pellets are used in a modified epalrestat composition of the present invention. In a further embodiment, at least three types of epalrestat pellets are used in a composition. In this embodiment, an immediate release pellet, and multiple modified release pellets are used, wherein the modified release pellets differ in the number of polymer coatings applied to the respective pellets. In yet another embodiment, immediate release pellets are not used in the compositions of the invention, but at least two types of modified release pellets are used. In a further embodiment, the first modified release pellet is coated once with a water insoluble layer and the second modified release pellet is coated twice with a water insoluble layer.

The water insoluble polymer employed in the modified release coating(s), in one embodiment, is selected from one or more of the following compounds: polymethacrylate, methacrylic acid copolymers, methacrylate ester copolymers, acrylic acid, cellulose esters, cellulose ethers, or cellulose ester-ethers such as ethyl cellulose, cellulose acylate, cellulose deacylate, cellulose triacylate, cellulose acetate, cellulose acetate butyrate, cellulose diacetate, cellulose triacetate, mono- di- and tri-cellulose arylates, and the like. Additional water insoluble polymers for forming the outer coating comprise cellulose acetaldehyde dimethyl acetate, cellulose acetate ethylcarbamate, cellulose acetate methylcarbonate, cellulose dimethylaminoacetate, semipermeable polyamide, polyvinyl acetate, semipermeable polyurethanes, semipermeable sulfonated polystyrenes, cross-linked selectively semipermeable polymers formed by the coprecipitation of an anion and a cation. Mixtures of the aforementioned polymers may also be employed.

In one embodiment, where multiple water insoluble polymer layers are applied to the pellet, each layer comprises a distinct water insoluble polymer. In another embodiment, each layer comprises the same water insoluble polymer.

Once the extended release coating is applied, as discussed above, one or more additional coatings can be applied as desired. In one embodiment no additional coatings are applied. Surfactants and or plasticizers may also be applied, in any of the coatings. The surfactant, in one embodiment, is selected from anionic, cationic, amphoteric and nonionic surfactants, including dialkyl sodium sulfosuccinate, polyoxyethylene glycerol, polyoxyethylene steryl ether, propoxy-ethoxy copolymer, polyoxyethylene fatty alcohol ester, polyoxyethylene sorbitan fatty acid esters, ethoxylated hydrogenated castor oil and butoxylated hydrogenated castor oil.

Swellable Matrices

In one embodiment, the modified release epalrestat composition is formulated by employing a pharmaceutically acceptable water swellable polymer, together with epalrestat or a derivative thereof. Optionally, the formulation can comprise sodium alginate, as described in U.S. Pat. No. 5,811,126, hereby incorporated by reference in its entirety.

Suitable water swellable polymers for use with the present invention include hydrophilic or hydrophobic polymers, such as gums, cellulose ethers and protein derived materials. In one embodiment, at least one cellulose ether is employed, e.g., a hydroxyalkylcellulose or a carboxyalkylcellulose. In a further embodiment, the cellulose ether is hydroxyethylcellulose, hydroxypropylcellulose or hydroxypropylmethylcellulose, or a combination thereof.

Other suitable materials include digestible, long chain ($C_8$-$C_{50}$) substituted or unsubstituted hydrocarbon derivatives, such as fatty acids, fatty alcohols, glyceryl esters of fatty acids, mineral oil and waxes. The hydrocarbons derivatives, in one embodiment, have a melting point between 25° C. and 90° C.

Without wishing to be bound by theory, upon oral ingestion and contact with gastrointestinal fluids, the swellable matrix modified release epalrestat compositions of the present invention are believed to swell and gel to form a matrix from which epalrestat, or the pharmaceutically acceptable epalrestat derivative, is released. Since epalrestat is suspended or distributed throughout the composition and consequently throughout the matrix, a constant amount of epalrestat (or derivative) can be released per unit time in vivo by dispersion or erosion of the outer portions of the matrix.

Epalrestat Prodrugs

In one embodiment, modified release of epalrestat is achieved through covalently attaching a prodrug moiety to epalrestat or derivative thereof. For example, the prodrug moiety can be an ester, amino acid, or a peptide.

Further Components of the Modified Release Pharmaceutical Compositions

As described above, there are multiple ways in which to achieve a modified release composition of the present invention. The modified release composition may be sustained release, extended release, time release or controlled release.

The composition may also be formulated to provide a mono-modal or bi-modal release profile. By "mono-modal", it is meant a composition comprising a modified-release (MR) component. By "bi-modal", it is meant a composition comprising both an immediate-release (IR) component and a MR component. The bi-modal composition provides an initial burst of epalrestat, or a pharmaceutically acceptable derivative thereof, for a quick build up of the systemic level of epalrestat in order to, for instance, exert the therapeutic effects, followed by the modified release of epalrestat, or a pharmaceutically acceptable derivative thereof, for maintaining the therapeutic level. After the IR component quickly releases epalrestat, or a pharmaceutically acceptable derivative thereof, the MR component releases the drug thereafter over a longer period of time, such as over about 1 to about 48 hours, preferably over about 2 hours to 36 hours, and more preferably over about 3 to about 24 hours for maintaining the therapeutic level of epalrestat.

The epalrestat or epalrestat derivative employed in the present invention may be used in combination with other therapies and/or active agents. Accordingly, the present invention provides, in one embodiment, a pharmaceutical composition comprising at least one compound useful in the practice of the present invention, or a pharmaceutically acceptable derivative thereof (e.g., salt, solvate, cocrystal, etc.), a second active agent, and, optionally a pharmaceutically acceptable carrier or excipient.

When combined in the same formulation, it will be appreciated that the epalrestat or epalrestat derivative are preferably stable in the presence of, and compatible with each other and the other components of the formulation.

The present invention includes pharmaceutical compositions comprising a compound of the invention adapted for use in human or veterinary medicine. Such compositions may be presented for use in a conventional manner with the aid of one or more suitable carriers. A carrier, for the purposes of this invention, is also an excipient. Acceptable carriers for therapeutic use are well-known in the pharmaceutical art, and are described, for example, in Remington's Pharmaceutical Sciences, Mack Publishing Co. (A. R. Gennaro edit. 1985). The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may also be used.

The compounds used in the invention may be milled using known milling procedures such as wet milling to obtain a particle size appropriate for tablet formation and for other formulation types. Finely divided (nanoparticulate) preparations of the compounds may be prepared by processes known in the art, see, e.g., International Patent Application No. WO 02/00196 (SmithKline Beecham).

The compounds and pharmaceutical compositions of the present invention, in one embodiment, are administered orally (e.g., as a tablet, sachet, capsule, pastille, pill, bolus, powder, paste, granules, bullets or premix preparation, ovule, elixir, solution, suspension, dispersion, gel, syrup or as an ingestible solution). In addition, compounds may be present as a dry powder for constitution with water or other suitable vehicle before use, optionally with flavoring and coloring agents. Solid and liquid compositions may be prepared according to methods well-known in the art. Such compositions may also contain one or more pharmaceutically acceptable carriers and excipients which may be in solid or liquid form.

Dispersions can be prepared in a liquid carrier or intermediate, such as glycerin, liquid polyethylene glycols, triacetin oils, and mixtures thereof. The liquid carrier or intermediate can be a solvent or liquid dispersive medium that contains, for example, water, ethanol, a polyol (e.g., glycerol, propylene glycol or the like), vegetable oils, non-toxic glycerine esters and suitable mixtures thereof. Suitable flowability may be maintained, by generation of liposomes, administration of a suitable particle size in the case of dispersions, or by the addition of surfactants.

The compositions of the invention may contain excipients to allow for modified release, as described above. Additionally, the compositions of the invention may contain one or more additional excipients that do not contribute to modified release of epalrestat. In one embodiment, the modified release compositions comprise at least one excipient in addition to the components necessary for modified release. In a further embodiment, the excipient is selected from microcrystalline cellulose, lactose, sodium citrate, calcium carbonate, dibasic calcium phosphate and glycine, disintegrants such as starch (e.g., corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

Examples of pharmaceutically acceptable disintegrants for oral compositions useful in the present invention include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and crosslinked polyvinylpyrrolidone.

Examples of pharmaceutically acceptable binders for oral compositions useful herein include, but are not limited to, acacia, cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions useful herein include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulfate.

Examples of pharmaceutically acceptable lubricants useful in the compositions of the invention include, but are not limited to, magnesium stearate, talc, polyethylene glycol, polymers of ethylene oxide, sodium lauryl sulfate, magnesium lauryl sulfate, sodium oleate, sodium stearyl fumarate, and colloidal silicon dioxide.

Examples of suitable pharmaceutically acceptable odorants for the oral compositions include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include, but are not limited to, synthetic and natural dyes such as titanium dioxide, beta-carotene and extracts of grapefruit peel.

Suitable examples of pharmaceutically acceptable sweeteners for the oral compositions include, but are not limited to, aspartame, saccharin, saccharin sodium, sodium cyclamate, xylitol, mannitol, sorbitol, lactose and sucrose.

Suitable examples of pharmaceutically acceptable buffers useful herein include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants useful herein include, but are not limited to, sodium lauryl sulfate and polysorbates.

Solid compositions of a similar type may also be employed as fillers in gelatin capsules. Excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Suitable examples of pharmaceutically acceptable stabilizers and antioxidants include, but are not limited to, ethylenediaminetetraacetic acid (EDTA), thiourea, tocopherol and butyl hydroxyan In embodiments of the present invention, the modified release composition comprises epalrestat or a pharmaceutically acceptable derivative thereof; and one or more water-swellable polymers. In another embodiment, the sustained release composition further comprises a release rate adjusting agent. When administered to a patient on a regular dosing schedule, the sustained release composition provides to the patient a therapeutic effect continuously over the period of the regular dosing schedule. That is, the therapeutic effect, once attained after the first administration, is constant during the period of the regular dosing schedule which includes multiple dosing intervals. The regular schedule can be a dosing regimen provided by instructions accompanying the sustained release composition product. For example, such dosing regimen can be fixed or variable amount of the sustained release composition taken once per day or twice per day, two times per week, three times per week, or four times per week.

In embodiments of the present invention, the modified release composition, when administered to a patient on a regular dosing schedule, provides a relatively flat plasma concentration profile of epalrestat at steady state, wherein there are no substantial peak or trough in the relatively flat plasma concentration profile and the minimum plasma concentration of epalrestat in the relatively flat plasma concentration profile is sufficient to provide a therapeutic effect to the patient.

In one embodiment of the present invention, the modified release composition, when administered to a patient on a regular dosing schedule, provides a relatively flat plasma concentration profile of epalrestat at steady state such that a mean $C_{min}/C_{max}$ epalrestat ratio during the dosing interval is about 0.55 to about 1.0, about 0.6 to about 1.0, or about 0.65 to about 1.0, or about 0.7 to about 1.0, or about 0.75 to about 1.0, or about 0.8 to about 1.0, or about 0.85 to about 1.0, or about 0.9 to about 1.0, or about 0.95 to about 1.0 and the $C_{min}$ is sufficient to provide a therapeutic effect.

In one embodiment of the present invention, the modified release composition, when administered to a patient once or twice a day, provides a therapeutic effect for at least about 8 hours and a mean $C_8/C_{max}$ epalrestat ratio of about 0.55 to about 1.0, about 0.6 to about 1.0, or about 0.65 to about 1.0, or about 0.7 to about 1.0, or about 0.75 to about 1.0, or about 0.8 to about 1.0, or about 0.85 to about 1.0, or about 0.9 to about 1.0, or about 0.95 to about 1.0 at steady state after administration to the patient.

In one embodiment of the present invention, the modified release composition, which is in a once or twice a day dosage form, provides to a patient a therapeutic effect for about 12 to about 24 hours and a relatively flat plasma concentration profile of epalrestat at steady state such that the minimum plasma concentration of epalrestat during the dosing interval is about 55%, 60%, 65%, 70%, 75%, 80%, 85%, 90%, or 95% of the maximum plasma concentration during the dosing interval.

In one embodiment of the present invention, the modified release composition, which in one embodiment, is in a once or twice a day dosage form, provides to a patient a therapeutic effect for about 12 hours to about 24 hours and a relatively flat plasma concentration profile of epalrestat at steady state such that the maximum plasma concentration of epalrestat during the dosing interval is about 145%, 140%, 135%, 130%, 125%, 120%, 115%, 110%, or 105% of the minimum plasma concentration during the dosing interval.

In embodiments of the present invention, the modified release composition comprises epalrestat or a pharmaceutically acceptable derivative thereof; a water-swellable and pH independent polymer; an anionic non-cellulose-based water-swellable polymer; and a release rate adjusting agent, such as a saccharide-based polymer. In another embodiment, the sustained release composition further comprises one or more pharmaceutically acceptable excipient.

The water-swellable and pH independent polymer refers to a hydrophilic polymer which swells to form a gel when exposed to an aqueous medium and its solubility in water does not substantially change according to the pH of the aqueous environment. The water-swellable and pH independent polymer can be any cellulose ether polymer, i.e., a polymer derived from partial or complete etherification of the hydroxyl groups in a cellulose molecule. Examples of cellulose ether polymer include, but are not limited to hypromellose, hydroxypropyl ethyl celluloses, hydroxypropyl cellulose, hydroxyethyl cellulose, methyl cellulose, and combinations thereof.

The anionic non-cellulose-based water-swellable polymer denotes a hydrophilic polymer which carries anionic charges in a pH neutral environment, is not derived fro cellulose, and swells to form a gel when exposed to an aqueous medium. Examples of anionic non-cellulose-based water-swellable polymer include, but are not limited to anionic derivatives of agar; anionic derivatives of guar gum; anionic derivatives of locust bean gum; anionic derivatives of xanthan gum; anionic derivatives of alginin (such as alginates); anionic derivatives of polysaccharides of mannose and galactose, or chitosan; anionic derivatives of modified starch; and combinations thereof.

The release rate adjusting agent refers to a compound which can modify the release rate of the active ingredient upon gellation of the hydrophilic polymers. Such release rate adjusting agent can be a compound derived from a saccharide, i.e., saccharide-based. For example, the release rate adjusting agent can be a polyol compound which derives from saccharides (mono- or poly-saccharides) via reduction, such as hydrogenation. A polyol compound is also known as sugar alcohol which includes, but is not limited to arabitol, xylitol, ribitol, mannitol, sorbitol, dulcitol, fucitol, iditol, isomalt, maltitol, lactitiol, and combinations thereof.

In embodiments of the present invention, the modified (e.g., sustained) release composition is in a matrix form, i.e., a solid dosage form comprising a matrix. As used herein, the term "matrix" denotes a homogeneous solid mixture composed of evenly dispersed ingredients throughout. In one embodiment, the matrix comprises epalrestat or a pharmaceutically acceptable derivative thereof; a water-swellable and pH independent polymer; an anionic non-cellulose-based water-swellable polymer; and a release rate adjusting agent, such as a saccharide-based polymer. In another embodiment, the matrix further comprises one or more pharmaceutically acceptable excipient. In one example, the matrix is in form of an oral tablet.

In one embodiment of the sustained release composition, the weight ratio of the water-swellable and pH independent polymer to the anionic non-cellulose-based water-swellable polymer is from about 2.5:1 to about 1.5:1, or about 2.3:1 to about 1.7:1, or about 2.2:1 to about 1.8:1, about 2.1:1 to about 1.9:1, or about 2:1.

In one embodiment of the sustained release composition, the weight ratio of the water-swellable and pH independent polymer to the polyol compound is from about 1.5:1 to about 1:1.5, or about 1.3:1 to about 1:1.3, or about 1.2:1 to about 1:1.2, or about 1.1:1 to about 1:1.1, or about 1:1.

In one embodiment of the sustained release composition, the weight ratio of the anionic non-cellulose-based water-swellable polymer to the polyol compound is from about 1:2.5 to about 1:1.5, or about 1:2.3 to about 1:1.7, or about 1:2.2 to about 1:1.8, about 1:2.1 to about 1:1.9, or about 1:2.

In one embodiment of the sustained release composition, the weight ratio of the water-swellable and pH independent polymer to the anionic non-cellulose-based water-swellable polymer to the polyol sugar or osmotic agent is about 2:1:2.

In one embodiment of the sustained release composition, epalrestat or a pharmaceutically acceptable derivative thereof is in an amount of about 10% to about 45%, or about 30% to about 45%, or about 34% to about 43%, or about 35% to about 42%, or about 37% to about 40% weight percentage. In one embodiment of the sustained release composition, the water-swellable and pH independent polymer is in an amount of about 18% to about 33%, or about 20% to about 31%, or about 22% to about 29%, or about 24% to about 27% weight percentage. In one embodiment of the sustained release composition, the release rate adjusting agent, such as the polyol compound, is in an amount of about 18% to about 33%, or about 20% to about 31%, or about 22% to about 29%, or about 24% to about 27% weight percentage. In one embodiment of the sustained release composition, the anionic non-cellulose-based water-swellable polymer is in an amount of about 9% to about 16.5%, or about 10% to about 15.5%, or about 11% to about 14.5%, or about 12% to about 13.5% weight percentage.

Epalrestat or a pharmaceutically acceptable derivative thereof in the sustained release composition can be any of the epalrestat species including all of the isomers, salts, solvates, and derivatives thereof. In one embodiment of the sustained release composition, epalrestat or a pharmaceutically acceptable derivative thereof is choline hydrogen diepalrestat or betaine hydrogen diepalrestat. In one embodiment of the sustained release composition, epalrestat or a pharmaceutically acceptable derivative thereof comprises epalrestat isomer 1, epalrestat isomer 2, epalrestat isomer 3, and/or epalrestat isomer 4. In one embodiment of the sustained release composition, epalrestat or a pharmaceutically acceptable derivative thereof is a crystalline salt of epalrestat selected from the group consisting of a potassium anhydrate salt, a sodium anhydrate salt and a 1-(2-hydroxyethyl)-pyrrolidine anhydrate salt.

The modified release composition may further optionally comprises one or more pharmaceutically acceptable excipient, such as lubricant and/or glidant. The one or more pharmaceutically acceptable excipient, such as lubricant and/or glidant, can be any of those known in the pharmaceutical art. Exemplary excipients include microcrystalline cellulose or powdered cellulose, which can act as compression aids; low molecular weight methyl cellulose (e.g., having a number average molecular weight from about 1000 to about 30,000), ethylcellulose, low molecular weight hydroxypropyl cellulose (e.g., having a number average molecular weight from about 1000 to about 50,000), low molecular weight hydroxypropyl methylcellulose (e.g., having a number average molecular weight from about 9000 to about 30,000 and a viscosity from about 1 to about 50 mPa s for a 2% (w/v) aqueous solution at 20° C.), polyvinyl alcohol, polyvinyl acetate, dicalcium phosphate, titanium dioxide, talc, alumina, starch, kaolin, polacrilin potassium, low molecular weight polyvinyl pyrrolidone (e.g., having a number average molecular weight from about 1000 to about 30,000), hydroxyethyl cellulose, sugar polyols, monosaccharides, disaccharides, polysaccharides, or a combination comprising at least one of the foregoing additional excipients.

The lubricant can be any substance capable of reducing friction by making surfaces smooth or slippery. Examples of suitable lubricants include the alkaline earth metal salts of solid fatty acids (for example the alkaline earth metal salts of fatty acids having from about 16 to about 22 carbon atoms), particularly the magnesium and calcium salts of stearic acid (e.g. magnesium stearate), sodium stearyl fumarate, zinc stearate, glyceryl behenate, talc, or a combination comprising one or more of the foregoing lubricants.

The glidant can be any substance that enhances the flow of a granular mixture by reducing interparticle friction and that is used in the pharmaceutical production of tablets, capsules, pellets, etc. Examples of suitable glidants include silicon dioxide (AEROSIL, Degussa), fumed or colloidal silica. The glidant can be present in the matrix in amounts of up to about 10 wt %, specifically about 0.25 to about 5 wt %, and more specifically about 0.5 to about 1 wt % of the total weight of the controlled-release composition.

The pharmaceutical compositions of the invention may contain from 0.01 to 99% weight per volume of the epalrestat or epalrestat derivative.

Dosages

Appropriate subjects to be treated according to the methods of the invention include any human or animal in need of such treatment. It is within the skill of the ordinary practitioner in the art (e.g., a medical doctor or veterinarian) to determine if a subject is in need of treatment with epalrestat. The subject is preferably a mammal, more preferably a human, but can be any subject or animal, including a laboratory animal in the context of a clinical trial, screening, or activity experiment employing an animal model. Thus, as can be readily appreciated by one of ordinary skill in the art, the methods and compositions of the present invention are particularly suited to administration to any animal or subject, particularly a mammal, and including, but not limited to, domestic animals, such as feline or canine subjects, farm animals, such as but not limited to bovine, equine, caprine, ovine, and porcine subjects, research animals, such as mice, rats, rabbits, goats, sheep, pigs, dogs, cats, etc., avian species, such as chickens, turkeys, songbirds, etc.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Depending on the severity of the disorder/disease/indication to be treated, a suitable therapeutically effective and safe dosage, as may readily be determined within the skill of the art, can be administered to subjects. For oral administration to humans, the daily dosage level of the epalrestat may be in single or divided doses. However, in one embodiment, the subject is administered a single daily dose. The duration of treatment may be determined by one of ordinary skill in the art, and should reflect the nature of the disease or indication to be treated, and/or the rate and degree of therapeutic response to the treatment. Typically, a physician will determine the actual dosage which will be most suitable for an individual subject.

In one embodiment, the epalrestat formulation of the invention is administered at a once daily dose of 25 mg, 50 mg, 100 mg, 150 mg, 200 mg or 250 mg epalrestat or diepalrestat.

Administration

The modified release compositions of the present invention may be administered by methods known by those of ordinary skill in the art. For example, the compositions can be administered enterally (e.g., oral administration) or parenterally. Parenteral administration includes, but is not limited to, the following routes of administration: intravenous, intraarterial, intramuscular, intracisternal, intracerebral.

In one embodiment, the modified release compositions of the present invention are administered orally. The oral composition may be solid or non-solid. The non-solid, in one embodiment, is a solution of epalrestat or a suspension of epalrestat.

Methods of the Invention

In the methods of the invention, the epalrestat modified release composition is, in one embodiment, administered once daily. However, the invention is not limited thereto.

In one embodiment, the modified release composition is formulated for twice-a-day administration. In another embodiment, the modified release composition is administered every other day, or six times per week, or five times per week, or four times per week, or three times per week, or two times per week, or once per week.

In one embodiment, the present invention is directed to a method of inhibiting aldose reductase in a subject in need thereof. The method comprises administering an effective amount of a modified release composition of epalrestat, or derivative thereof, to the subject. In a further embodiment, the epalrestat in the modified release formulation is selected from the group consisting of epalrestat isomer 1, epalrestat isomer 2, epalrestat isomer 3 and epalrestat isomer 4. In a further embodiment, the epalrestat is epalrestat isomer 1 and is the choline hydrogen diepalrestat cocrystal. This cocrystal is described in PCT publication No. WO 2010/028132, hereby incorporated by reference in its entirety. The epalrestat used in this method can be any epalrestat described herein, or known to those of ordinary skill in the art.

Epalrestat and its derivatives are useful for treating and/or preventing diabetic complications including, for example, diabetic neuropathy, diabetic nephropathy, diabetic cardiomyopathy, diabetic retinopathy, diabetic gastroparesis, cataracts, foot ulcers, diabetic macroangiopathy, diabetic microangiopathy, high blood glucose and high HbA1c levels.

Accordingly, in one embodiment, the present invention provides a method for the treatment of a diabetic complication in a subject in need thereof. The diabetic complication is selected from diabetic neuropathy, diabetic nephropathy, diabetic cardiomyopathy, diabetic retinopathy, diabetic gastroparesis, cataracts, foot ulcers, diabetic macroangiopathy, diabetic microangiopathy, high blood glucose and high HbA1c levels. The method comprises administering to the subject an effective amount of a modified release composition of epalrestat, or a pharmaceutically acceptable derivative thereof. In a further embodiment, the epalrestat or pharmaceutically acceptable derivative thereof in the modified release formulation is selected from the group consisting of epalrestat isomer 1, epalrestat isomer 2, epalrestat isomer 3 and epalrestat isomer 4. In a further embodiment, the epalrestat is epalrestat isomer 1 and is present in a choline hydrogen diepalrestat cocrystal. In another embodiment, the epalrestat is a crystalline salt of epalrestat, for example, a potassium anhydrate salt, a sodium anhydrate salt, or a 1-(2-hydroxyethyl)-pyrrolidine anhydrate salt.

In one embodiment of the invention, a method is provided for treating cardiac tissue ischemia in a subject in need thereof. The method comprises administering to the subject an effective amount of a modified release epalrestat composition. The composition may comprise epalrestat or a derivative thereof. For example, epalrestat may be present as a salt, crystal, co-crystal, sovate or hydrate. In a further embodiment, the epalrestat or derivative thereof in the modified release formulation is selected from the group consisting of epalrestat isomer 1, epalrestat isomer 2, epalrestat isomer 3 and epalrestat isomer 4. In a further embodiment, the epalrestat is epalrestat isomer 1 and is present in a choline hydrogen diepalrestat cocrystal. In another embodiment, the epalrestat is a crystalline salt of epalrestat, for example, a potassium anhydrate salt, a sodium anhydrate salt, or a 1-(2-hydroxyethyl)-pyrrolidine anhydrate salt.

In yet another embodiment, a method is provided for the treatment of an indication selected from myocardial protection during surgery, myocardial protection in patients presenting with ongoing cardiac or cerebral ischemic events, chronic cardioprotection in patients diagnosed with, or at risk for, coronary heart disease, cardiac dysfunction or myocardial stunning, neurodegenerative disease (of the CNS and/or PNS), neuropathies associated with toxicity (neurotoxicity) such as chemotherapy (i.e., vincristine or cisplatin-induced motor neuropathy) and alcohol consumption, immune-mediated neurodiseases such as multiple sclerosis (MS) and Guillain-Barre syndrome, hereditary neuropathies such as Charcot-Marie-Tooth neuropathies (see Lebo et al. (1992). *Am. J. Hum. Genet.* V. 50, pp. 42-55), injury due to trauma, and compromised function due to senescence. Examples of neurodegenerative disorders include but are not limited to, Huntington's disease, amyotrophic lateral sclerosis (ALS), Alzheimer's disease, Parkinson's disease, and Shy-Drager syndrome. The method comprises administering to the subject an effective amount of a modified release epalrestat composition. The composition may comprise epalrestat or a derivative thereof. For example, epalrestat may be present as a salt, crystal, co-crystal, sovate or hydrate. In a further embodiment, the epalrestat or derivative thereof in the modified release formulation is selected from the group consisting of epalrestat isomer 1, epalrestat isomer 2, epalrestat isomer 3 and epalrestat isomer 4. In a further embodiment, the epalrestat is epalrestat isomer 1 and is present in a choline hydrogen diepalrestat cocrystal. In even a further embodiment, the modified release composition comprises an additional crystal form of epalrestat, for example a crystal form disclosed in WO 2010/011926 or WO 2010/011922.

EXAMPLES

The present invention is further illustrated by reference to the following Examples. However, it should be noted that these Examples, like the embodiments described above, are illustrative and are not to be construed as restricting the scope of the invention in any way.

Example 1

Physical Characterization Of Choline Hydrogen Diepalrestat

Table 1 provides properties of the choline hydrogen diepalrestat drug substance.

TABLE 1

Characterization of the choline hydrogen diepalrestat drug substance.

| | |
|---|---|
| Chemical Name | Choline hydrogen diacid cocrystal of 5-[(1Z,2E)-2-methyl-3-phenylpropenylidene]-4-oxo-2-thioxo-3-thiazolidineacetic acid |
| Molecular Formula | $C_{35}H_{39}N_3O_7S_4$ |
| Molecular Weight | 741.96 g/mol |
| Structural Formula | 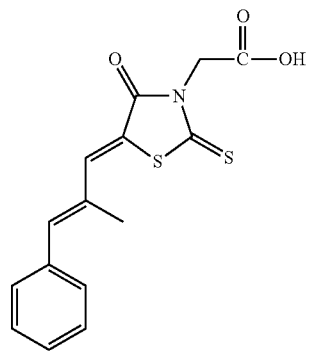 [SMILES: CC(/C=C1\SC(=S)N(CC(=O)O)C1=O)=C\c1ccccc1] 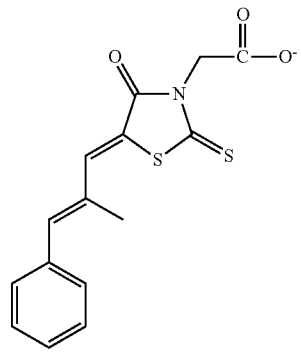 [SMILES: CC(/C=C1\SC(=S)N(CC(=O)[O-])C1=O)=C\c1ccccc1] |

TABLE 1-continued

Characterization of the choline hydrogen diepalrestat drug substance.

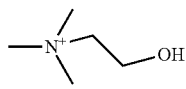

| | |
|---|---|
| Physical Description | Yellow to bright yellow solid. |
| Solubility | insoluble in water and freely soluble in dichloromethane and ethanol |
| Melting point | About 212° C. to about 213° C. |
| Stability | Unstable in light |

The solubility of choline hydrogen diepalrestat was tested in buffer solutions [please provide the components of the buffer solutions] of varying pH. The results are provided below, in Table 2.

TABLE 2

Choline hydrogen diepalrestat solubility in buffers of varying pH

| Different pH media | Solubility (mg/ml) |
|---|---|
| pH 1.2 buffer | -Nil- |
| pH 3.0 buffer | -Nil- |
| pH 4.5 buffer | -Nil- |
| pH 5.0 buffer | 0.02 mg/ml |
| pH 6.8 buffer | 0.46 mg/ml |
| pH 7.2 buffer | 0.31 mg/ml |
| Purified water | 0.14 mg/ml |

Example 2

Manufacture Of Choline Hydrogen Diepalrestat Compositions

Tables 3-6 provide the components of various choline hydrogen diepalrestat compositions of the invention.

TABLE 3

| Ingredients | Brand name | Batch Size: 100 g (equivalent to 200 tablets) Batch CHT1-001/044 mg/tablet | % Qty | Batch Size: 50 g (equivalent to 100 tablets) Batch CHT1-001/015 mg/tablet | % Qty | Batch Size: 50 g (equivalent to 100 tablets) Batch CHT1-001/020 mg/tablet | % Qty | Batch Size: 47.2 g (equivalent to 100 tablets) Batch CHT1-001/026 mg/tablet | %Qty |
|---|---|---|---|---|---|---|---|---|---|
| Core Composition | | | | | | | | | |
| Intra granular materials | | | | | | | | | |
| Choline Hydrogen Diepalrestat | — | 174.22* | 34.8 | 174.22 | 39.82 | 174.22 | 34.84 | 174.22 | 36.91 |
| Mannitol USP/BP/EP | Pearlitol 200 SD/ Mannogem EZ SD/Pearlitol 160C | 127.28 | 25.5 | 127.3 | 29.10 | 127.3 | 25.46 | 127.08 | 26.92 |
| Hypromellose K-4 M | Methocel K-4 M or K15M | 125.00 | 25.00 | 125.0 | 28.57 | 187.5 | 37.50 | 125.00 | 26.48 |
| Sodium alginate | Keltone HVCR | 62.50 | 12.50 | — | — | — | — | 31.25 | 6.62 |
| Purified water | — | 230.5 | — | N/A. These formulations undergo a direct compression process. | | | | | |
| Pre-lubrication: | | | | | | | | | |
| Colloidal Silicon dioxide | Cabosil M5 | 2.50 | 0.50 | 2.50 | 0.57 | 2.5 | 0.50 | 2.50 | 0.53 |
| Purified talc EP/BP | — | 2.50 | 0.50 | 2.50 | 0.57 | 2.5 | 0.50 | 2.50 | 0.53 |
| Lubrication: | | | | | | | | | |
| Hydrogenated vegetable oil | Lubritab | 6.00 | 1.20 | 6.0 | 1.37 | 6.0 | 1.20 | 9.45 | 2.00 |
| Total | | 500.0 | 100.0 | 437.5 | 100.0 | 500.0 | 100.0 | 472.0 | 100.0 |

TABLE 3-continued

| Ingredients | Brand name | Batch Size: 50 g (equivalent to 100 tablets) Batch CHT1-001/032 | | Batch Size: 50 g (equivalent to 100 tablets) Batch CHT1-001/038 | | Batch Size: 50 g (equivalent to 100 tablets) Batch CHT1-001/002 | |
|---|---|---|---|---|---|---|---|
| | Core Composition | mg/tablet | % Qty | mg/tablet | % Qty | mg/tablet | % Qty |
| | | Intra granular materials | | | | | |
| Choline Hydrogen Diepalrestat | — | 174.22 | 34.84 | 174.22 | 34.84 | 174.22 | 34.8 |
| Mannitol USP/BP/EP | Pearlitol 200 SD/ Mannogem EZ SD/ Pearlitol 160C | 236.65 | 47.33 | 221.03 | 44.21 | 127.3 | 25.5 |
| Hypromellose K-4 M | Methocel K-4 M or K15M | 15.63 | 3.125 | 31.25 | 6.25 | 125.0 | 25.0 |
| Sodium alginate | Keltone HVCR | 62.50 | 12.50 | 62.50 | 12.50 | 62.5 | 12.5 |
| Purified water | — | N/A. These formulations undergo a direct compression process. | | | | | |
| | | Pre-lubrication: | | | | | |
| Colloidal Silicon dioxide | Cabosil M5 | 2.5 | 0.50 | 2.5 | 0.50 | 2.50 | 0.50 |
| Purified talc EP/BP | — | 2.5 | 0.50 | 2.5 | 0.50 | 2.50 | 0.50 |
| | | Lubrication: | | | | | |
| Hydrogenated vegetable oil | Lubritab | 6.00 | 1.20 | 6.00 | 1.20 | 6.00 | 1.2 |
| | Total | 500.0 | 100.0 | 500.0 | 100.0 | 500.0 | 100.0 |

*174.22 mg of Choline hydrogen diepalrestat is equivalent to 150 mg of Diepalrestat.

TABLE 4

| Ingredients | Brand name/ Supplier | B. No: 074 | | B. No: 074-A | | B. No: 074-B | | B. No CHT1-001/068 | | B. No CHT1-001/050 | |
|---|---|---|---|---|---|---|---|---|---|---|---|
| | | mg/tab | % Qty | mg/tab | % Qty | mg/Tab | % Qty | mg/Tab | % Qty | mg/Tab | % Qty |
| Sized granules of B. No CHT1-001/068 | — | 304.5 | 63.84 | 304.5 | 56.59 | 304.5 | 59.85 | | | | |
| Choline Hydrogen Diepalrestat* | | | | | | | | 174.22 | 41.98 | 174.22 | 36.52 |
| Mannitol fine powder | | | | | | | | 124.28 | 29.95 | 127.08 | 36.52 |
| | | Binder | | | | | | | | | |
| Hydroxy propyl cellulose-LF | Klucel LF | | | | | | | 6.0 | 1.45 | 3.00 | 0.63 |
| Purified Water | | | | | | | | Q.S. | | 57.00 | Q.S |
| | | Extra granular materials | | | | | | | | | |
| Hypromellose K-4 M | Methocel K-4M | — | — | 62.50 | 20.53 | 31.25 | 6.14 | 62.50 | 15.06 | 125.00 | 26.20 |
| Hypromellose K-100 LV CR | Methocel K-100 LV CR | 125.00 | 26.21 | 125.00 | 41.05 | 125.0 | 24.57 | — | — | — | — |
| Eudragit L100-55 | Eudragit L100-55 | 31.25 | 6.55 | 31.25 | 5.79 | 2.50 | 6.14 | 31.25 | 7.53 | 31.25 | 6.55 |
| Colloidal silicon dioxide | Cabosil M5 | 2.50 | 0.52 | 2.50 | 0.82 | 4.75 | 0.49 | 2.50 | 0.60 | 2.50 | 0.52 |
| | | Lubrication | | | | | | | | | |
| Hydrogenated vegetable oil | Lubritab | 4.75 | 1.00 | 4.75 | 1.56 | 4.42 | 0.93 | 4.75 | 1.14 | 4.72 | 0.99 |
| Purified talc | Luzenac | 4.75 | 1.00 | 4.75 | 1.56 | 4.75 | 0.93 | 4.75 | 1.14 | 4.65 | 0.97 |
| Magnesium stearate | Ferro | 4.75 | 1.00 | 4.75 | 1.56 | 4.75 | 0.93 | 4.75 | 1.14 | 4.65 | 0.97 |
| | Total | 477.5 | 100 | | 100 | | 100 | 415.00 | 100.0 | 477.07 | 100.0 |

TABLE 5

| Ingredients | Brand name/ Supplier | B. Size 177.12 gm equivalent to 328 tabs B. No CHT1-001/074-A | | B. Size 1620 gm equivalent to 3000 tabs B. No CHT1-001/092 | |
|---|---|---|---|---|---|
| | | mg/tab | % Qty | mg/tab | % Qty |
| Core Composition | | | | | |
| Intra granular materials | | | | | |
| Choline Hydrogen Diepalrestat* | — | 174.22* | 32.26 | 174.22* | 32.26 |
| Mannitol powder USP | Pearlitol 160C | 124.28 | 23.01 | 124.28 | 23.01 |
| Binder | | | | | |
| Hydroxy propyl cellulose - LF | Klucel LF | 6.00 | 1.11 | 6.00 | 1.11 |
| Purified water | — | 70.77 | Q.S | 49.33 | Q.S |
| Extra granular materials | | | | | |
| Hypromellose K-4 M | Methocel K-4M | 62.50 | 11.57 | 62.50 | 11.57 |
| Hypromellose K-100 LV CR | Methocel K-100 LV CR | 125.00 | 23.15 | 125.00 | 23.15 |
| Methacrylic acid copolymer Type C, NF | Eudragit L100-55 | 31.25 | 5.79 | 31.25 | 5.79 |
| Colloidal silicon dioxide - NF | Aerosil | 2.50 | 0.46 | 2.50 | 0.46 |
| Lubrication | | | | | |
| Hydrogenated vegetable oil -NF | Lubritab | 4.75 | 0.88 | 4.75 | 0.88 |
| Purified talc - EP/BP | Signet | 4.75 | 0.88 | 4.75 | 0.88 |
| Magnesium stearate - EP/USP/NF | Ferro | 4.75 | 0.88 | 4.75 | 0.88 |
| Total | | 540.00 | 100.00 | 540.00 | 100.00 |

TABLE 6

| | Concentration of polymer (mg/unit) | | | Core weight of tablet | Granulation |
|---|---|---|---|---|---|
| B. No | K-4 M | K-15 M | Sod. Alginate | (mg) | Process |
| 002 | 125.0 | — | 62.50 | 500.0 | Direct compression |
| 015 | 125.0 | — | — | 437.5 | |
| 020 | 187.5 | — | — | 500.0 | |
| 026 | 125.0 | — | 31.25 | 472.0 | |
| 032 | — | 15.63 | 62.50 | 500.0 | |
| 038 | — | 31.25 | 62.50 | 500.0 | |
| 044 | 125.0 | — | 62.50 | 500.0 | Wet granulation |

The 001/044 batch was manufactured by the following wet granulation process. Choline hydrogen diepalrestat, mannitol (Pearlitol 200 SD), hypromellose (Methocel K4M) and sodium alginate were added together and mixed in a black polybag for 10 minutes. The dry mixed material transferred into a stainless steel (SS) bowl. Purified water (23.8 g) was added to the dry mixed material in the SS bowl as a binding solution, and the mixture was granulated manually for 3 minutes. An additional 22.3 g of purified water was subsequently added, followed by manual granulation of the mixture for 4 minutes. The wet granules were passed through a #16 mesh sieve and were dried in a tray dryer at 50° C. for 80 minutes. The dried granules were passed through a #30 mesh sieve and the retention was rasped manually. Colloidal silicon dioxide and purified talc were sifted through #60 mesh, added to the dried granules, and mixed to form a granulated mixture in a 'Y' blender, attached with a 500 cc plastic container (14 RPM, 10 minutes). Hydrogenated vegetable oil (Lubritab) was sifted through #60 mesh and then added to the granulated mixture.

Wet granulation is not necessary in producing the epalrestat formulations of the invention. For example, choline hydrogen diepalrestat, mannitol, Hypromellose K4M and sodium alginate were sifted through #40 mesh (420 microns) and mixed in a double lined black poly bag for 10 minutes. Colloidal silicon dioxide and talc were sifted through #60 mesh and added to the choline hydrogen diepalrestat/mannitol/Hypromellose K4M/sodium alginate mixture, and further mixed. Hydrogenated vegetable oil (Lubritab) was sifted through #60 mesh and then added to the mixture. The mixture is then compressed, as described further below.

In another process, choline hydrogen diepalrestat, mannitol and hypromellose K4M were sifted through #40 mesh (420 microns) and mixed in a double lined black poly bag (CHT1-01/015; CHT1-001/020). For these batches, sodium alginate was not used. Colloidal silicon dioxide and talc were sifted through #60 mesh and added to the choline hydrogen diepalrestat/mannitol/hypromellose K4M mixture, and further mixed. Hydrogenated vegetable oil was sifted through #60 mesh and then added to the mixture.

The CHT1-001/074 batches were made according to the following table (Table 7):

TABLE 7

| B. No: CHT1-001/074 | B. No: CHT1-001/074 - A | B. No: CHT1-001/074 - B | Blending time | RPM |
|---|---|---|---|---|
| Extra granular materials | | | | |
| Pre Lubrication | | | | |
| Sized granules + sifted materials of Hypromellose K - 100 LV prem, Methyl methacrylic acid co-polymer (Eudragit L100-55) and colloidal silicon dioxide | Sized granules + sifted materials of Hypromellose K-4M CR, Hypromellose K - 100 LV prem, Methyl methacrylic acid co-polymer (Eudragit L100-55) and colloidal silicon dioxide | | 20 minute | 14 |
| Lubrication | | | | |
| Pre lubricated materials + Sifted materials of Hydrogenated vegetable oil, Purified talc, magnesium stearate | Pre lubricated materials + Sifted materials of Hydrogenated vegetable oil, Purified talc, magnesium stearate | | 10 minute | 14 |

Specifically, CHT1-001/074 and CHT1-001/092 batches were made as follows: Choline hydrogen diepalrestat, mannitol were sifted through #18 mesh and loaded into RMG and dry mixed for 5 minutes with impeller at fast speed and chopper off. Klucel-LF was dispersed in water under stirring. Stirring was continued until a clear solution was obtained. The binder solution was added into RMG and granulated with slow impeller speed and chopper fast. Kneading was continued until to get desired granules. The wet mass was unloaded from RMG, and was passed through Co-mill with 4.5 mm screen.

The granules were then dried at the inlet temperature of 65° C. for 30 minutes (L.O.D=Less than 1%). The dried granules were passed through #18 mesh (1000 micron) and the retains were milled through multi-mill with Knife forward, medium speed fitted with 1.0 mm screen and it was passed through the #18 mesh (1000 micron).

The extra-granular materials of Hypromellose K—4 Premium CR, Hypromellose K-100 LV CR, Methyl methacrylic acid co-polymer (Eudragit L100-55) and colloidal silicon dioxide were sifted through #40 mesh (425 micron) mesh and the hydrogenated vegetable oil, purified talc, magnesium stearate, were sifted through #60 (250 microns) mesh separately.

The sized granules of step 8 were loaded in to the Y—Blender along with the sifted hypromellose K 100 LV CR, hypromellose K—4 premium CR, methyl methacrylic acid co-polymer (Eudragit L100-55) and colloidal silicon dioxide were added in to the blender and mixed for 20 minutes.

The sifted materials of hydrogenated vegetable oil, Purified talc, magnesium stearate were added in the above step and mixed for 10 minutes and unloaded into a double lined black color polyethylene bag.

Characteristics of various lubricated blends, described above, are provided in Table 8, below.

TABLE 8

| Parameter | CHT1-001/044 | CHT1-001/068 (sized granules) | CHT1-001/068 (lubricated) | CHT1-001/074 (lubricated) | CHT1-001/092 (sized granules) | CHT1-001/092 (lubricated) |
|---|---|---|---|---|---|---|
| Bulk density (g/ml) | 0.43 | 0.444 | 0.465 | 0.471 | 0.454 | 0.444 |
| Tapped density (g/ml) | 0.51 | 0.571 | 0.645 | 0.635 | 0.588 | 0.625 |
| Carr's index (%) | 15.686 | 22.222 | 27.907 | 25.882 | 22.789 | 28.960 |
| Hausner's Ratio | 1.186 | 1.286 | 1.387 | 1.349 | 1.295 | 1.408 |
| Loss on drying at 105° C. | 2.10% | 0.870 | 1.770 | 2.560 | 0.77 | 2.79 |

Compression of the Lubricated Blends

The blends were compressed in a 16-station compression machine (Cad-mach). The lubricated blends were weighed (as a target theoretical weight of 472.00 mg/unit or 500.00 mg/unit) and transferred in to the die cavity manually using 14.1 mm×6.7 mm caplet shape punches and suitable dies. Tablets were compressed without pre-compression force. The properties of the compressed tablets are provided in Table 9 and Table 10, below.

TABLE 9

| Tablet Parameter | CHT1-001/044 (wet granulation) | CHT1-001/002 | CHT1-001/002-A | CHT1-001/002-B* | CHT1-001/015 | CHT1-001/020 | CHT1-001/026 |
|---|---|---|---|---|---|---|---|
| Average Weight (mg) | 500.1 (492.3-503.2 mg) | 503 (492-508) | 502 (494-511) | 507 (494-512) | 439.5 (431.3-450.1) | 504.3 (489.9-521.3) | 473.3 (468.3-481.2) |

TABLE 9-continued

| | | | | | | | |
|---|---|---|---|---|---|---|---|
| Thickness (mm) | 5.85 (5.77-5.94) | 5.49 (5.45-5.57) | 5.08 (5.04-5.15) | 5.49 (5.45-5.57) | 4.77 (4.64-4.89) | 5.62 (5.44-5.78) | 5.07 (5.02-5.14) |
| Hardness (N) | 180 N (138-212 N) | 194 (160-246) | 287 (271-318) | 125 (90-138) | 190 (159-220) | 217 (131-271) | 204 N (193-221 N) |
| Friability (%) | Nil | 0.104 | 0.122 | 0.216 | | | |
| Description/ Appearance | Yellow colored, caplet shaped uncoated tablets, plain on both the sides. | | | | | | |

| Tablet Parameter | CHT1-001/032 | CHT1-001/038 | CHT1-001/050 | CHT1-001/068 | CHT1-001/074 | CHT1-001/074-A | CHT1-001/074-B |
|---|---|---|---|---|---|---|---|
| Average Weight (mg) | 500.7 (491.9-505.5) | 499.7 (494.8-502.5) | 478.1 (475.1-481.3) | 415.8 (413.6-418.4) | 477.02 (472.9-478.4) | 541.7 (538.0-544.1) | 506.1 (505.1-509.8) |
| Thickness (mm) | 5.31 (5.28-5.39) | 5.35 (5.33-5.36) | 4.96 (4.93-4.97) | 4.47 (4.45-4.50) | 5.31 (5.30-5.34) | 6.23 (6.20-6.27) | 5.71 (5.64-5.81) |
| Hardness (N) | 180 (169-189) | 181 (138-215) | 174 (165-193) | 185 (178-195) | 181 (162-190) | 170 (152-179) | 167 (139-190) |
| Friability (%) | 0.081 | 0.084 | 0.08 | 0.020% | Nil | 0.04% | 0.14% |
| Description/ Appearance | Yellow colored, caplet shaped uncoated tablets, plain on both the sides. | | | | | | |

*CHT1-001/002-B includes 500 mg lubricated blend of CHT1-001/002 and 6.0 mg calcium chloride. For this batch, calcium chloride was triturated using mortar and pestle and sifted through #100 mesh sieve. The sifted Calcium chloride was added to the lubricated blend of B. No CHT1-001/002 and mixed in a double lined black poly bag.

TABLE 10

| Parameters | B. No. CHT1-001/074 - A | B. No. CHT1-001/092 |
|---|---|---|
| Punch dimension | 14.1 × 6.7 mm caplet shape punches | 17.0 × 6.5 mm Plain on both the punches |
| Tablet Description/Appearance | Yellow to dark yellow color caplet shape tablets plain on both sides. | |
| Average Weight of the tablets (mg) | 541.7 (538.0-544.1) | 540.9 (537.4-546.1) |
| Thickness of the tablets (mm) | 6.23 (6.20-6.27) | 5.46 (5.41-5.51) |
| Hardness of the tablets (N) | 170 (152-179) | 181 (175-188) |
| Friability of the tablets (% w/w) | 0.04% | 0.007% |

Example 3

Coating Of Diepalrestat Tablets

Two different coatings were tested. The components of the coatings are provided below, in Table 11, below.

B.No: CHT1-001/092: PVA based film coating with an aqueous system. B.No: CHT1-001/098: Seal coating with organic system followed by PVA based film coating with aqueous system.

TABLE 11

| Ingredients | B. No: CHT1-001/092, Batch size: 1500 tablets Qty per tab. (mg) | B. No: CHT1-001/098, Batch size: 1500 tablets Qty per tab. (mg) |
|---|---|---|
| Seal coating composition | | |
| Opadry clear 59000 | — | 8.10 |
| Isopropyl alcohol | — | 53.8 |
| Dichloro methane | — | 53.8 |
| Seal coated tablet weight | — | 548.1 |
| Solid content in the dispersion | — | 7% |
| Film coating composition | | |
| Opadry yellow 85F520040 | 16.20 | 16.44 |
| Purified water | 64.8 | 65.76 |
| Film coated tablet weight | 556.20 | 564.54 |
| Solid content in the dispersion | 20% | 20% |

Preparation of Seal Coating Dispersion

Opadry clear 59000 was dispersed in isopropyl alcohol, then a sufficient quantity of dichloromethane was added into it to solubilize the Opadry clear coating material.

Preparation of Film Coating Dispersion

Opadry yellow 85F520040 was dispersed into a sufficient quantity of purified water (to make a 20% dispersion) under stirring and the stirring was continued for 45 minutes.

The coating parameters and process are provided below.

Capacity of Coating Pan used: 5 kg.

Loading quantity: 2 kg

No. of spray gun used: 1 No.

Nozzle diameter: 1.2 mm

Inlet temperature: 55±5° C.

Atom. Pressure: 3.0-3.5 bar

TABLE 12

| Parameters | B. No: CHT1-001/092 film coating | B. No: CHT1-001/098 seal coating | B. No: CHT1-001/098 film coating |
|---|---|---|---|
| Inlet temperature (° C.) | 54-56° C. | 48.0-56.0° C. | 54.0-56.0° C. |
| Cabinet temperature (° C.) | 40-54° C. | 42.0-46.0° C. | 40.0-45.0° C. |
| Exhaust temperature (° C.) | 43-48° C. | 46.0-52.0° C. | 42.0-48.0° C. |
| Pan speed (RPM) | 2-8 | Inch - 8.0 | Inch - 10 |
| Pump speed (RPM) | 1-3 | 2-3 | 1-2 |
| Atomization pressure (psi) | 3.0-3.5 | 3.0-3.5 | 3.5 |
| Total processing time | 2 Hours | 2 hours 15 minutes | 2 hours 40 minutes |

TABLE 13

| Parameters | B. No. CHT1-001/092 (Film Coated) | B. No. CHT1-001/098 (Seal coating) | B. No. CHT1-001/098 (Seal + Film Coated) |
|---|---|---|---|
| Tablet Description | Pale yellow to peach color caplet shape tablets plain on both sides. | | |
| Average Weight (mg) | 557.9 (552.8-563.5) | 545.3 (538.7-551.4) | 561.0 (554.5-570.9) |
| Thickness (mm) | 5.54 (5.49-5.58) | 5.52 (5.49-5.56) | 5.61 (5.56-5.65) |
| Hardness (N) | 229 (218-246) | 194 (174-218) | 241 (223-257) |

Dissolution profiles for the coated tablets are provided in Table 14, below.

TABLE 14

Medium: pH 6.8 phosphate buffer, Volume: 900 ml, Apparatus: USP type-I, RPM: 100

| Time (hr) | Target - 2 (18 Hr profile) | B. No: 074-A Core | B. No: 092 Core | B. No: 092 Coated | B. No: 098 Coated |
|---|---|---|---|---|---|
| 0 | 0 | 0 | 0 | 0 | 0 |
| 1 | 8 | 4 | 5 | 3 | 3 |
| 2 | 13 | 7 | 10 | 8 | 8 |
| 3 | 19 | 12 | 17 | 14 | 15 |
| 4 | 24 | 18 | 26 | 20 | 23 |
| 6 | 35 | 34 | 45 | 35 | 40 |
| 8 | 46 | 49 | 62 | 49 | 55 |
| 10 | 57 | 63 | 75 | 63 | 67 |
| 12 | 68 | 73 | 84 | 72 | 78 |
| 14 | 78 | 82 | 88 | 74 | 85 |
| 15 | 84 | 86 | 93 | 83 | 87 |
| 16 | 89 | 89 | 98 | 88 | 91 |
| 18 | 100 | 95 | 97 | 94 | 97 |
| 20 | — | 96 | 102 | 98 | 100 |
| 24 | — | 104 | — | — | — |
| F1 | | 8.12 | 16.41 | 7.32 | 10.52 |
| F2 | | 65.8 | 49.34 | 67.89 | 60.02 |

Figure 4:
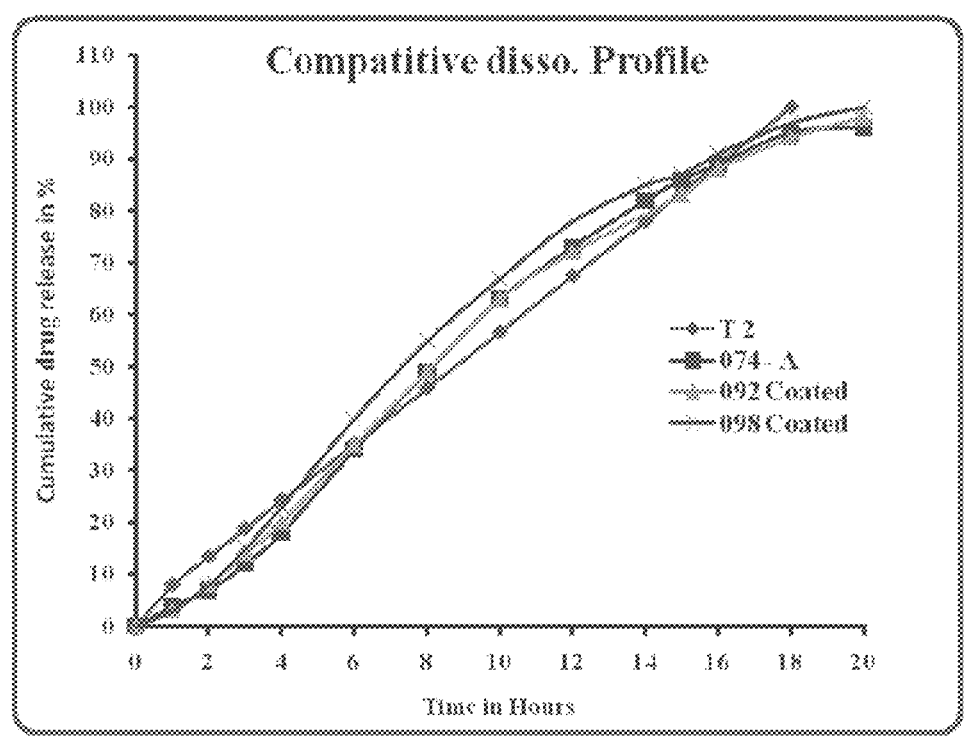
FIG. 4 is a graph showing the dissolution of tablets of the present invention compared to a 18 hr. target release profile.
Figure 5:
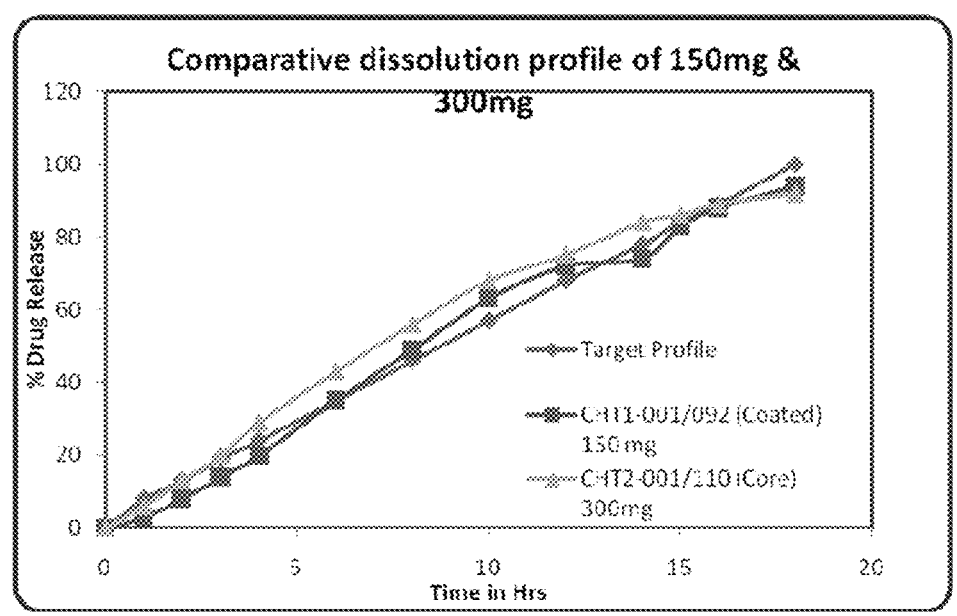
FIG. 5 is a graph showing the dissolution profile of 150 mg and 300 mg diepalrestat tablets of the present invention compared to a target release profile.

The dissolution profile of the coated tablets of B.No CHT1-001/092 appears similar as that of the targeted profile (see Table 14 and FIG. 4). Table 15 and FIG. 5 provide the dissolution profile for diepalrestat modified release tablets of the present invention.

TABLE 15

| Time (hr.) | Target Profile | CHT1-001/092 150 mg (Coated) | CHT2-001/110 300 mg (Core) |
|---|---|---|---|
| 0 | 0 | 0 | 0 |
| 1 | 8 | 3 | 6 |
| 2 | 13 | 8 | 13 |
| 3 | 19 | 14 | 20 |
| 4 | 24 | 20 | 29 |
| 6 | 35 | 35 | 43 |
| 8 | 46 | 49 | 56 |
| 10 | 57 | 63 | 68 |
| 12 | 68 | 72 | 75 |
| 14 | 78 | 74 | 84 |
| 15 | 84 | 83 | 86 |
| 16 | 89 | 88 | 89 |
| 18 | 100 | 94 | 92 |
| 20 | — | 98 | 98 |
| F1 | — | 7.32 | 9.86 |
| F2 | — | 67.89 | 59.65 |

Example 4

Hydrogen Diepalrestat Tablet Core Intactness Study

Tablets were placed in petri dish filled with purified water. One tablet was removed at 2 hour intervals and washed under running water until the intact core was exposed. The study continued until the complete core was hydrated. Results are provided in Table 16, below.

The results indicate that core intactness is not dependent on the hardness. Tablets with calcium chloride showed faster erosion during initial stages and erosion slowed down during later stage with more gel strength. The tablets with calcium chloride may exhibit faster release up to 4 hours and followed by more sustained release.

TABLE 16

| Time | Batch No. CHT1-001/002 | Batch No. CHT1-001/002-A | Batch No. CHT1-001/002-B |
|---|---|---|---|
| 2 Hours | 1) Initially slow erosion was observed then viscous gel layer formed around the tablet. 2) Intact core was observed after washing. | | 1) Initially tablet eroded faster than the previous two batches then viscous gel layer formed around the tablet. 2) Intact core was observed after washing. |

TABLE 16-continued

| Time | Batch No. CHT1-001/002 | Batch No. CHT1-001/002-A | Batch No. CHT1-001/002-B |
|---|---|---|---|
| 4 Hours | | Intact core was observed after washing. | Gel strength was found less as compared to previous two batches. Intact core was observed after washing. |
| 6 Hours | | 1) Gradual erosion was observed in the tablets, 1 mm unwetted core was observed. 2) It seems that, the percentage erosion not depended on hardness | 1) Swelling & Gel strength was more as compare to batches without calcium chloride. 2) Core was found intact after washing. |
| 8 Hours | | Very small intact core was observed. | 1) Swelling & Gel strength was more as compare to batches without calcium chloride. 2) Loosely packed granules were found which was not hydrated. |
| 10 Hours | | No core was found intact, completely hydrated. | No intact core was observed. As in comparison with batches without calcium chloride, gel strength found more. |

Example 5

Hydrogen Diepalrestat Tablet Dissolution and Solubility Studies

Saturation solubility studies were performed for the API in buffer solutions differing in pH. The results are given below in Table 17. No solubility was observed for the drug in pH 1.2, 3.0 and 4.5 buffers. The highest drug solubility was observed in pH 6.8 buffer.

TABLE 17

| pH of Media | Solubility (mg/ml) |
|---|---|
| pH 1.2 buffer | -Nil- |
| pH 3.0 buffer | -Nil- |
| pH 4.5 buffer | -Nil- |
| pH 5.0 buffer | 0.02 mg/ml |
| pH 6.8 buffer | 0.46 mg/ml |
| pH 7.2 buffer | 0.31 mg/ml |
| Purified water | 0.14 mg/ml |

Dissolution studies on the hydrogen diepalrestat modified release tablets of the present invention were carried out in 900 mL phosphate buffer, pH 6.8, using the USP type I (Basket) apparatus at 100 RPM. Data was collected at the following timepoints (hr): 1, 2, 3, 4, 6, 8, 10, 12, 16, 20 and 24. Where indicated (see Table 10), dissolution was also tested in change over media, where the pH was varied as follows: pH 1.2 (0-2 hrs.)→pH 4.5 (2-20 hrs.)→pH 6.8 (20-24 hrs.).

The release profiles of various tablets were compared to a target release profile, which was calculated based on the available literature regarding pharmacokinetics followed by thrice daily administration of epalrestat 50 mg IR formulation. The results are provided in Table 18 (24 hr. target release profile) and Table 19 (15 and 18 hr. target release profiles), below.

FIG. 1 also provides the results of one study, where the dissolution of a CHT1-001/002-A tablet was tested in different media, and compared to a target drug release profile. It was found that faster dissolution occurred in media pH 6.8 phosphate buffer. Additionally, in change over media, no drug release was observed in pH 1.2 buffer up to 2 hours. As provided above in Table 9, at pH 1.2, the API is not soluble.

It was found that batches with different concentration of Methocel K 15 M CR (3.125 & 6.25% w/w) showed faster release profile from the initial time points (CHT1-001/032, CHT1-001/038).

Regarding the tablets that did not include sodium alginate (CHT1-001/015 and CHT1-001/020), no significant difference was found in the drug release between. Accordingly, different concentration of Methocel polymer (29.57% w/w and 37.50% w/w) did not effect the release profile. However, the release profile for both batches was not comparable to the target drug release.

The batch taken with wet granulation process (CHT1-001/044) showed controlled release in the initial time points (up to 4 hours) and was followed by a faster release profile.

Figure 2:
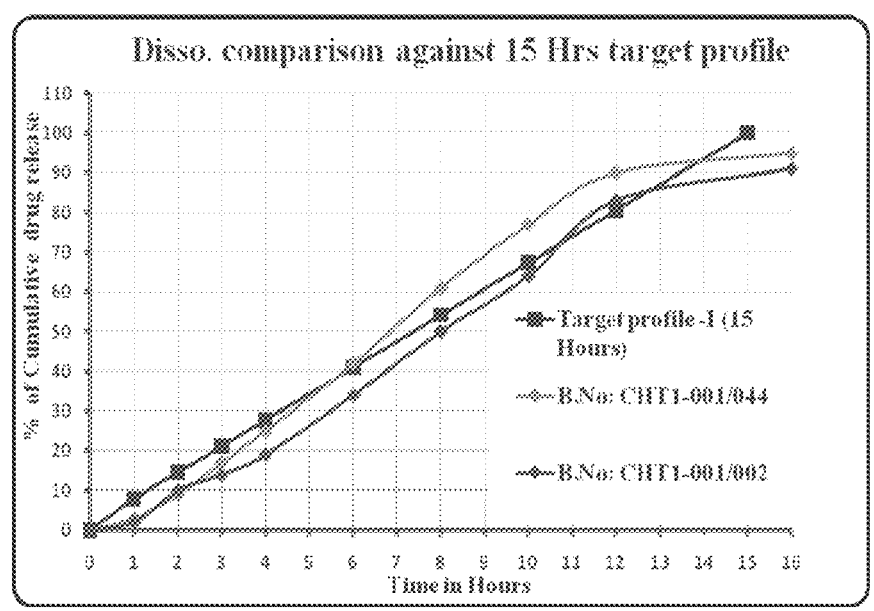
FIG. 2 is a graph showing the dissolution of tablets of the present invention compared to a 24. hr. target release profile.
Figure 3:
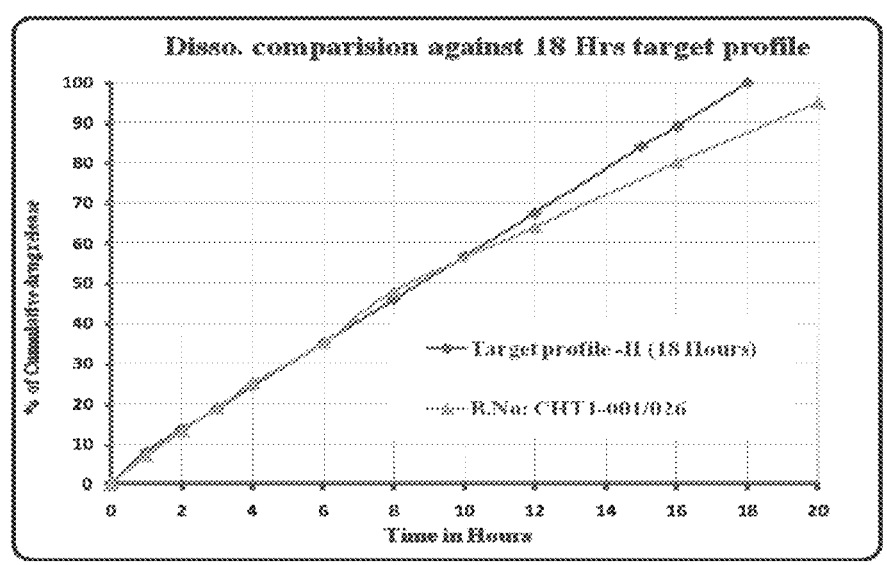
FIG. 3 is a graph showing the dissolution of tablets of the present invention compared to a 18 hr. target release profile.

FIG. 2 and FIG. 3 show the release profile of various tablets, compared to the target 15 hr. release profile (FIG. 2) and target 18-hr. release profile (FIG. 3).

TABLE 18

| Time (hr.) | Target drug release | Batch number: CHT1-001/002-A pH 6.8 Phosphate buffer | Batch number: CHT1-001/002-A Change over media | Batch number: CHT1-001/032 pH 6.8 Phosphate buffer | Batch number: CHT1-001/038 pH 6.8 Phosphate buffer | Batch number: CHT1-001/044 pH 6.8 Phosphate buffer | Batch number: CHT1-001/015 pH 6.8 Phosphate buffer | Batch number: CHT1-001/020 pH 6.8 Phosphate buffer | Batch number: CHT1-001/026 pH 6.8 Phosphate buffer |
|---|---|---|---|---|---|---|---|---|---|
| 1 | 8.0 | 2.0 | 0.0 | 33 | 21 | 3 | 1 | 3 | 7.0 |
| 2 | 12.0 | 10.0 | 0.0 | 61 | 44 | 9 | 9 | 5 | 13.0 |
| 3 | 16.0 | 14.0 | 2.0 | 85 | 69 | 17 | 11 | 8 | 19.0 |
| 4 | 20.0 | 19.0 | 4.0 | 98 | 88 | 25 | 12 | 11 | 25.0 |
| 6 | 28.0 | 34.0 | 14.0 | 99 | 99 | 42 | 14 | 15 | 35.0 |
| 8 | 36.0 | 50.0 | 20.0 | 98 | 96 | 61 | 17 | 19 | 48.0 |
| 12 | 52.0 | 64.0 | 35.0 | 98 | 97 | 90 | 22 | 27 | 64.0 |

TABLE 18-continued

| Time (hr.) | Target drug release | Batch number: CHT1-001/002-A pH 6.8 Phosphate buffer | Batch number: CHT1-001/002-A Change over media | Batch number: CHT1-001/032 pH 6.8 Phosphate buffer | Batch number: CHT1-001/038 pH 6.8 Phosphate buffer | Batch number: CHT1-001/044 pH 6.8 Phosphate buffer | Batch number: CHT1-001/015 pH 6.8 Phosphate buffer | Batch number: CHT1-001/020 pH 6.8 Phosphate buffer | Batch number: CHT1-001/026 pH 6.8 Phosphate buffer |
|---|---|---|---|---|---|---|---|---|---|
| 16 | 68.0 | 83.0 | 51.0 | 99 | — | 95 | 34 | 31 | 80.0 |
| 20 | 84.0 | 91.0 | 74.0 | 98 | — | 93 | 35 | 39 | 95.0 |
| 24 | 100.0 | 97.0 | 85.0 | — | — | 99 | 41 | 37 | 101.0 |

TABLE 19

Comparative dissolution profile of Diepalrestat MR tablets 150 mg
Condition: Medium: pH 6.8 phosphate buffer, Volume: 900 ml, Apparatus: USP type-I, RPM: 100 RPM, Cumulative drug release in Percentage (%)

| | Target drug release | | B. | | | | | | | | | | | |
|---|---|---|---|---|---|---|---|---|---|---|---|---|---|---|
| Time (hr.) | Target-I 15 Hour | Target-II 18 Hour | B. No-002 | B. No-010** | B. No-015 | B. No-020 | B. No-026 | B. No-032 | B. No-038 | B. No-044 | B. No-050 | B. No-68 | B. No-74 | B. No-74-A | B. No-74-B |
| 0 | 0 | 0 | 0 | 0 | 0 | 0 | 0 | 0 | 0 | 0 | 0 | 0 | 0 | 0 | 0 |
| 1 | 8 | 8 | 2 | 4 | 1 | 3 | 7 | 33 | 21 | 3 | 4 | 6 | 7 | 4 | 5 |
| 2 | 15 | 13 | 10 | 10 | 9 | 5 | 13 | 61 | 44 | 9 | 6 | 11 | 16 | 7 | 10 |
| 3 | 21 | 19 | 14 | 17 | 11 | 8 | 19 | 85 | 69 | 17 | 8 | 18 | 27 | 12 | 16 |
| 4 | 28 | 24 | 19 | 21 | 12 | 11 | 25 | 98 | 88 | 25 | 11 | 29 | 39 | 18 | 24 |
| 6 | 41 | 35 | 34 | 38 | 14 | 15 | 35 | 99 | 99 | 42 | 18 | 58 | 62 | 34 | 41 |
| 8 | 54 | 46 | 50 | 60 | 17 | 19 | 48 | 98 | 96 | 61 | 25 | 75 | 79 | 49 | 55 |
| 10 | 67 | 57 | 64 | 76 | — | — | — | — | — | 77 | 31 | 83 | 89 | 63 | 66 |
| 12 | 81 | 68 | 83 | 87 | 22 | 27 | 64 | 98 | 97 | 90 | 38 | 89 | 96 | 73 | 74 |
| 15 | 100 | 84 | — | — | — | — | — | — | — | — | 47 | 92 | 100 | 82 | 81 |
| 16 | — | 89 | 91 | 90 | 34 | 31 | 80 | 99 | — | 95 | 49 | 91 | 101 | 86 | 85 |
| 18 | — | 100 | — | — | — | — | — | — | — | — | 55 | 95 | 100 | 89 | 87 |
| 20 | — | — | 97 | 94 | 35 | 39 | 95 | 98 | — | 93 | 64 | 99 | 99 | 95 | 91 |
| 24 | — | — | — | 96 | 41 | 37 | 101 | — | — | 99 | 71 | — | — | 96 | 97 |

**B. No-010 is identical to B. No. except the source of the API is different (Shasun API for the 010 batch AMRI API for the 002 batch.

Example 6

Diepalrestat Ionization Study In Different pH Environments

The percentage ionization of Epalrestat in different pH environments of the human gastrointestinal tract was calculated based on the pKa value (3.61). The results are provided below, in Table 20.

The results indicate that the maximum percentage of drug exists in unionized state between pH 1.2 to 3.5, especially pH 1-3. Accordingly, it is thought that absorption will be higher at this pH range. Since solubility is lower in the pH range of 1-4.5, the drug may not be absorbed even if it is exist in unionized form.

The dissolution results for Aldonil tablets 50 mg (IR epalrestat formulation, data not shown) demonstrated negligible drug release at pH 1.2 media and only 12% release at pH 4.5 media.

$T_{max}$ for the IR formulation followed by oral administration is about 2.05±0.99, 2.25±0.95 h. It clearly indicates that, drug shall be absorbed in the lower pH (pH 1-3.5) without addition of any solubilizer in the formulation.

TABLE 20

| pH environment of the body | % Ionized |
|---|---|
| pH 1.2 | 0 |
| pH 3.0 | 20.0 |
| pH 3.5 | 44.0 |
| pH 4.0 | 71.0 |
| pH 4.5 | 89.0 |
| pH 5.0 | 96.0 |
| pH 5.5 | 99.0 |
| pH 6.0 | 100.0 |
| pH 6.8 | 100.0 |

Patents, patent applications, publications, product descriptions, and protocols which are cited throughout this application are incorporated herein by reference in their entireties.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention claimed is:

1. A modified release pharmaceutical composition, comprising
  epalrestat or a pharmaceutically acceptable derivative thereof;
  a water-swellable and pH independent polymer;
  an anionic non-cellulose-based water-swellable polymer; and
  a saccharide-based release rate adjusting agent.

2. The modified release pharmaceutical composition of claim 1, further comprising one or more pharmaceutically acceptable excipient.

3. The modified release pharmaceutical composition of claim 1, wherein the water-swellable and pH independent polymer is selected from the group consisting of hypromellose, hydroxypropyl ethyl celluloses, hydroxypropyl cellulose, hydroxyethyl cellulose, methyl cellulose, and combinations thereof.

4. The modified release pharmaceutical composition of claim 1, wherein the anionic non-cellulose-based water-swellable polymer is selected from the group consisting of anionic derivatives of agar; anionic derivatives of guar gum; anionic derivatives of locust bean gum; anionic derivatives of xanthan gum; anionic derivatives of alginin; anionic derivatives of polysaccharides of mannose and galactose, or chitosan; anionic derivatives of modified starch; and combinations thereof.

5. The modified release pharmaceutical composition of claim 1, wherein the saccharide-based release rate adjusting agent is a polyol compound.

6. The modified release pharmaceutical composition of claim 5, wherein the polyol compound is selected from arabitol, xylitol, ribitol, mannitol, sorbitol, dulcitol, fucitol, iditol, isomalt, maltitol, and lactitiol.

7. The modified release pharmaceutical composition of claim 1, which is in a matrix form.

8. The modified release pharmaceutical composition of claim 7, which is an oral tablet.

9. The modified release pharmaceutical composition of claim 1, wherein the weight ratio of the water-swellable and pH independent polymer to the anionic non-cellulose-based water-swellable polymer is from about 2.5:1 to about 1.5:1.

10. The modified release pharmaceutical composition of claim 5, wherein the weight ratio of the water-swellable and pH independent polymer to the polyol compound is from about 1.5:1 to about 1:1.5.

11. The modified release pharmaceutical composition of claim 5, wherein the weight ratio of the anionic non-cellulose-based water-swellable polymer to the polyol compound is from about 1:2.5 to about 1:1.5.

12. The sustained release pharmaceutical composition of claim 5, wherein the weight ratio of the water-swellable and pH independent polymer to the anionic non-cellulose-based water-swellable polymer to the polyol compound is about 2:1:2.

13. The modified release pharmaceutical composition of claim 1, wherein epalrestat or a pharmaceutically acceptable derivative thereof is in an amount of about 30% to about 45% weight percentage.

14. The modified release pharmaceutical composition of claim 1, wherein epalrestat or a pharmaceutically acceptable derivative thereof is choline hydrogen diepalrestat or betaine hydrogen diepalrestat.

15. A method for treating diabetes or a diabetic complication in a subject in need thereof, comprising administering to the subject the modified release pharmaceutical composition of claim 1.

16. The method of claim 15, wherein the modified release pharmaceutical composition is administered once per day or twice per day.

17. The method of claim 15, wherein the diabetic complication is selected from the group consisting of diabetic neuropathy, diabetic nephropathy, diabetic cardiomyopathy, diabetic retinopathy, diabetic gastroparesis, cataracts, foot ulcers, diabetic macroangiopathy, diabetic microangiopathy, high blood glucose, high HbA1c levels, and combinations thereof.

18. A method for inhibiting aldose reductase in a subject in need thereof, comprising administering to the subject the modified release pharmaceutical composition of claim 1.

19. The method of claim 18, wherein the modified release pharmaceutical composition is administered once per day or twice per day.

20. A method for affording cardioprotection in a subject in need thereof, comprising administering to the subject the modified release pharmaceutical composition of claim 1.

21. The method of claim 20, wherein the sustained release pharmaceutical composition is administered once per day or twice per day.

* * * * *